(12) United States Patent
Dariush

(10) Patent No.: US 7,386,366 B2
(45) Date of Patent: Jun. 10, 2008

(54) FEEDBACK ESTIMATION OF JOINT FORCES AND JOINT MOVEMENTS

(75) Inventor: Behzad Dariush, Sunnyvale, CA (US)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 57 days.

(21) Appl. No.: 11/481,700

(22) Filed: Jul. 5, 2006

(65) Prior Publication Data

US 2006/0282022 A1 Dec. 14, 2006

Related U.S. Application Data

(63) Continuation of application No. 10/151,647, filed on May 16, 2002, now Pat. No. 7,135,003.

(60) Provisional application No. 60/301,891, filed on Jun. 29, 2001, provisional application No. 60/353,378, filed on Jan. 31, 2002.

(51) Int. Cl.
*G06F 19/00* (2006.01)

(52) U.S. Cl. ............... 700/245; 700/189; 700/190; 700/217; 700/254; 700/258; 700/259; 700/260; 700/261; 700/262; 318/560; 318/568.1; 901/15; 901/16; 901/21; 901/39; 701/23

(58) Field of Classification Search ............... 700/189, 700/190, 217, 218, 245, 254, 258, 259, 260, 700/261, 262; 318/560, 568.1; 901/15, 901/16, 21, 39; 701/23

See application file for complete search history.

(56) References Cited

U.S. PATENT DOCUMENTS

| 4,244,120 A | 1/1981 | Harris |
| 4,786,847 A | 11/1988 | Daggett et al. |
| 4,834,200 A | 5/1989 | Kajita |
| 5,044,360 A | 9/1991 | Janke |

(Continued)

FOREIGN PATENT DOCUMENTS

RU 2 107 328 C1 3/1998

(Continued)

OTHER PUBLICATIONS

Wyeth, G. F., et al., "Distributed Digital Control of a Robot Arm," Proceedings of the Australian Conference on Robotics and Automation (ACRA 2000), Aug. 30-Sep. 1, 2000, pp. 217-222, [online] [retrieved on Dec. 31, 2006] Retrieved from the Internet: <URL: www.itee.uq.edu.au/~wyeth/Publications/puma.PDF>.

(Continued)

*Primary Examiner*—Khoi H. Tran
*Assistant Examiner*—McDieunel Marc
(74) *Attorney, Agent, or Firm*—Fenwick & West LLP; Mark Duell

(57) ABSTRACT

Apparatus and methods are provided for estimating joint forces and moments in human beings. A forward dynamics module determines simulated kinematic data. An error correction controller forces tracking error between the simulated kinematic data and measured (or desired) kinematic data to approach zero. The error correction controller generates a modified acceleration for input into an inverse dynamics module. The estimated joint forces and moments track the measured (or desired) kinematics without the errors associated with computing higher order derivatives of noisy kinematic data.

22 Claims, 24 Drawing Sheets

U.S. PATENT DOCUMENTS

| | | | |
|---|---|---|---|
| 5,136,227 A | 8/1992 | Nakano et al. | |
| 5,247,432 A | 9/1993 | Ueda | |
| 5,323,549 A | 6/1994 | Segel et al. | |
| 5,362,288 A | 11/1994 | Razon | |
| 5,432,417 A | 7/1995 | Takenaka et al. | |
| 5,459,659 A | 10/1995 | Takenaka | |
| 5,570,286 A | 10/1996 | Margolis et al. | |
| 5,625,577 A | 4/1997 | Kunii et al. | |
| 5,659,480 A | 8/1997 | Anderson et al. | |
| 5,706,589 A | 1/1998 | Marc | |
| 5,808,433 A | 9/1998 | Tagami et al. | |
| 5,835,693 A | 11/1998 | Lynch et al. | |
| 5,942,869 A | 8/1999 | Katou et al. | |
| 5,982,389 A | 11/1999 | Guenter et al. | |
| 6,045,524 A | 4/2000 | Hayashi et al. | |
| 6,076,025 A | 6/2000 | Ueno | |
| 6,152,890 A | 11/2000 | Kupfer et al. | |
| 6,161,080 A | 12/2000 | Aouni-Ateshian et al. | |
| 6,289,265 B1 | 9/2001 | Takenaka et al. | |
| 6,445,983 B1 | 9/2002 | Dickson et al. | |
| 6,505,096 B2 | 1/2003 | Takenaka et al. | |
| 6,580,969 B1 | 6/2003 | Ishida et al. | |
| 6,633,783 B1 | 10/2003 | Dariush et al. | |
| 6,640,160 B2 | 10/2003 | Takahashi et al. | |
| 6,750,866 B1 | 6/2004 | Anderson, III | |
| 6,766,204 B2 | 7/2004 | Niemeyer et al. | |
| 6,785,591 B1 | 8/2004 | Hansson | |
| 6,943,520 B2 | 9/2005 | Furuta et al. | |
| 7,010,390 B2 * | 3/2006 | Graf et al. | 700/245 |
| 7,013,201 B2 | 3/2006 | Hattori et al. | |
| 7,024,279 B2 * | 4/2006 | Rose et al. | 700/245 |
| 7,112,938 B2 | 9/2006 | Takenaka et al. | |
| 7,135,003 B2 | 11/2006 | Dariush | |
| 7,184,858 B2 * | 2/2007 | Okazaki et al. | 700/254 |
| 7,191,036 B2 * | 3/2007 | Takenaka et al. | 700/245 |
| 7,260,450 B2 * | 8/2007 | Okazaki et al. | 700/254 |
| 2003/0018283 A1 | 1/2003 | Dariush | |
| 2003/0023415 A1 | 1/2003 | Nakamura et al. | |
| 2004/0102723 A1 | 5/2004 | Horst | |
| 2004/0107780 A1 | 6/2004 | Kawai et al. | |
| 2004/0158175 A1 | 8/2004 | Ikeuchi et al. | |
| 2004/0193318 A1 | 9/2004 | Ito | |
| 2004/0249319 A1 | 12/2004 | Dariush | |
| 2004/0254771 A1 | 12/2004 | Riener et al. | |
| 2005/0102111 A1 | 5/2005 | Dariush et al. | |
| 2005/0104548 A1 | 5/2005 | Takenaka et al. | |
| 2005/0209535 A1 | 9/2005 | Dariush | |
| 2006/0046909 A1 | 3/2006 | Rastegar et al. | |
| 2006/0100818 A1 | 5/2006 | Nakamura et al. | |
| 2006/0139355 A1 | 6/2006 | Tak et al. | |

FOREIGN PATENT DOCUMENTS

| | | |
|---|---|---|
| WO | WO 00/35346 | 6/2000 |
| WO | WO 03/002054 | 1/2003 |

OTHER PUBLICATIONS

PCT International Search Report and Written Opinion, PCT/US06/22582, Feb. 2, 2007, 8 pages.

PCT International Search Report and Written Opinion, PCT/US05/11908, Mar. 8, 2007, 7 pages.

"Berkeley Researchers Developing Robotic Exoskeleton That Can Enhance Human Strength and Endurance,"ScienceDaily LLC, 1995-2004, [online] [Retrieved on Oct. 9, 2006] Retrieved from the Internet<URL:http://bleex.me.berkeley.edu/bleexhistPDFs/sciencedaily.pdf>.

Durfee, W.K., "Preliminary Design and Simulation of a Pneumatic, Stored-Energy, Hybrid Orthosis for Gait Restoration," Proceedings of IMECE04, 2004 ASME International Mechanical Engineering Congress, Nov. 13-20, 2004, [online] [Retrieved on Oct. 9, 2006] Retrieved from the Internet<URL: http://www.me.umn.edu/~wkdurfee/publications/IMECE2004-60075.pdf>.

International Search Report and Written Opinion, PCT/US06/11727, Nov. 9, 2006, 9 pages.

Isaacs, P.M. et al., "Controlling Dynamic Simulation with Kinematic Constraints, Behavior Functions, and Inverse Dynamics," Computer Graphics, Jul. 1987, pp. 215-224, vol. 21, No. 4.

Madigan, R.R., "Ankle-Foot Orthoses (AFO's) in Spastic Cerebral Palsy," Fillauer LLC, [online] [Retrieved on Oct. 9, 2006] Retrieved from the Internet<URL:http://www.fillauer.com/education/ED_afo.html#dynamic>.

Pratt, G.A. et al., "Active Orthotics for Helping the Neuromuscularly Impaired to Walk," [online] [Retrieved on Oct. 9, 2006] Retrieved from the Internet<URL:http://www.vcl.uh.edu/~rcv03/materials/grant/9733740.1064791086.pdf>.

"Regenerative Foot Braking," [online] [Retrieved on Oct. 9, 2006] Retrieved from the Internet<URL:http://www.halfbakery.com/idea/regenerative_20foot_20braking#1069693200>.

"Sensorless Fet Element DC Motor Driver," [online] [Retrieved on Oct. 9, 2006] Retrieved from the Internet<URL:http://robotx.sourceforge.net/bridge/bridge.shtml>.

Trost, F.J., "Energy-Storing Feet," JACPOC, 1989, vol. 24, No. 4, [online] [Retrieved on Oct. 9, 2006] Retrieved from the Internet<URL:http://jacpoc.oandp.com/library/1989_04_082.asp>.

Akhlaghi, F. et al., "In-shoe Biaxial Shear Force Measurement: the Kent Shear System," Medical & Biological Engineering & Computing, Jul. 1996, vol. 34, pp. 315-317.

Anderson, F. et al., "Static and Dynamic Optimization Solutions for Gait are Practically Equivalent", Journal of Biomechancis, 2001, vol. 34, pp. 153-161.

Anderson, F. et al., "Dynamic Optimization of Human Walking," *Journal of Biomechanical Engineering*, Oct. 2001, vol. 123, pp. 381-390.

Anderson, R. et al., "Numerical Differentiation Procedures for Non-Exact Data," Numererische Mathematik, 1974, vol. 22, pp. 157-182.

Baruh, H., Analytical *Dynamics*, Chapter 7, Rigid Body Kinematics, McGraw-Hill, 1999, pp. 355-371.

Burdea, G. et al., "Virtual Reality Technology", 1994, pp. 33-37, John Wiley and Sons, Inc.

Busby, H.R. et al., "Numerical Experiments With a New Differentiation Filter," Transactions of the ASME—Journal of Biomechanical Engineering, Nov. 1985, vol. 107, pp. 293-299.

Chao, E.Y. et al., "Application of Optimization Principles in Determining the Applied Moments in Human Leg Joints During Gait," J. Biomechanics, 1973, vol. 6, pp. 497-510, Pergamon Press, Great Britain.

Craig, J.J., "Nonlinear Control of Manipulators," Introduction to Robotics Mechanics and Control, $2^{nd}$, Ed., 1989, Chapter 10, pp. 333-361.

Crowninshield, R.D. et al., "A Physiologically Based Criterion Of Muscle Force Prediction In Locomotion," *Journal of Biomechanics*, vol. 14, No. 11, 1981, pp. 793-801.

Cullum, J., "Numerical Differentiation and Regularization," SIAM J. Numer. Anal., Jun. 1971, vol. 8, No. 2, pp. 254-265.

Dariush, B. et al., "Multi-Modal Analysis of Human Motion From External Measurements," Transactions of the ASME, Jun. 2001, vol. 123, pp. 272-278.

Dariush, B, "A Novel Algorithm For Generating A Forward Dynamics Solution To The Traditional Inverse Dynamics Problem," In *4th World Congress of Biomechanics*, Calgary, Canada, 2002.

Dariush, B., "A Forward Dynamics Solutions To Multi-Modal Inverse Dynamics Problems," In *International Society of Biomechanics*, XIXth Congress, Dunedin, NZ, 2003.

Dariush, B., "A Well-Posed, Embedded Constraint Representation of Joint Moments From Kinesiological Measurements," Journal of Biomechanical Engineering, Aug. 2000, vol. 122, pp. 437-445.

Delp, S. et al., "A Computational Framework for Simulating and Analyzing Human and Animal Movement," *IEEE Computing in Science and Engineering*; vol. 2, No. 5, 2000, pp. 46-55.

Dohrmann, C.R. et al., "Smoothing Noisy Data Using Dynamic Programming and Generalized Cross-Validation" Transactions of the ASME—Journal of Biomechanical Engineering, Feb. 1988, vol. 110, pp. 37-41.

Giakas, G. et al., "A Comparison of Automatic Filtering Techniques Applied to Biomechanical Walking Data," J. Biomechanics, 1997, vol. 00, No. 00, 4 pages.

Giakas, G. et al., "Optimal Digital Filtering Requires a Different Cut-Off Frequency Strategy for the Determination of the Higher Derivatives," J. Biomechanics, Apr. 1997, vol. 28, No. 00, 5 pages.

Grood, E.S. et al., "A Joint Coordinate System for the Clinical Description of Three Dimensional Motions: Application to the Knee," Journal of Biomechanical Engineering, 1983, pp. 136-144, No. 105.

Hatze, H. "The Use of Optimally Regularized Fourier Series for Estimating Higher-Order Derivatives of Noisy Biomechanical Data," J. Biomechanics, 1981, vol. 14, pp. 13-18.

Hemami, H. et al., "Modeling And Control Of Constrained Dynamic Systems With Application To Biped Locomotion In The Frontal Plane," IEEE Transactions on Automatic Control, vol. 4, No. 4, Aug. 1979, pp. 526-535.

Hemami, H., "A State Space Model for Interconnected Rigid Bodies," IEEE Trans. on Automatic Control, 1982, pp. 376-382, vol. 27, No. 2.

Hosein, R. et al., "A Study of In-shoe Plantar Shear in Normals," Clinical Biomechanics, 2000, vol. 15, pp. 46-53.

Jalics, L. et al., "A Control Strategy for Terrain Adaptive Bipedal Locomotion," Autonomous Robots, 1997, pp. 243-257, vol. 4.

Kawato, M., "Internal Models for Motor Control and Trajectory Planning," Current Opinion in Neurobiology, 1999, pp. 718-727, No. 9.

Khatib, O., A Unified Approach For Motion And Force Control Of Robot Manipulators: The Operational Space Formulation, *IEEE Journal of Robotics and Automation*, RA-3(1), 1987, pp. 43-53.

Klein, C. A. et al., Review Of Pseudoinverse Control For Use With Kinematically Redundant Manipulators, *IEEE Transactions on Systems, Man, and Cybernetics*, vol. 13, No. 2, 1983, pp. 245-250.

Piazza, S. et al., "Three-Dimensional Dynamic Simulation of Total Knee Replacement Motion During a Step-up Task," *Journal of Biomechanical Engineering*, vol. 123, 2001, pp. 599-606.

Runge, C.F. et al., "Estimating Net Joint Torques From Kinesiological Data Using Optimal Linear System Theory." IEEE Transactions on Biomedical Engineering, Dec. 1995, vol. 42, No. 12, pp. 1158-1164.

Simons, W. et al., "Differentiation of Human Motion Data Using Combined Spline and Least Squares Concepts," Journal of Biomechanical Engineering, Transactions of the ASME, Aug. 1991, vol. 113, pp. 348-351.

Thelen, D. et al., "Generating Dynamic Simulations of Movement Using Computed Muscle Control," *Journal of Biomechanics*, 36, 2003, pp. 321-328.

Vaughan, C. L. et al., "Appendix B., Detailed Mathematics Used in GaitLab," *Dynamics of Human Gait*, Second Edition, Kiboho Publishers, Cape Town South Africa, 1999, pp. 83-106.

Vukobratovic, M. et al., *Scientific Fundamentals of Robotics 7: Biped Loco-motion*. Springer-Verlag, 1990, pp. 17-27.

Winter, D.A., "Kinetics: Forces and Moments of Force," Biomechanics and Motor Control of Human Movement, 2nd Ed., New York, 1990, Chapter 4.

Wittenberg, J., *Dynamics of Systems of Rigid Bodies*, 1977, B.G. Teubner Stuttgart, 1977, p. 29-30.

Woltring, H.J., "A Fortran Package for Generalized, Cross Validatory Spline Smoothing and Differentiation," Adv. Eng. Software, 1986, vol. 8, No. 2, pp. 104-107.

Woltring, H.J., "On Optimal Smoothing and Derivative Estimation From Noisy Displacement Data in Biomechanics," Human Movement Science, vol. 4, 1985, pp. 229-245.

Agarwal, S.K. et al., "Theory and Design of an Orthotic Device for Full or Partial Gravity-Balancing of a Human Leg During Motion," IEEE Transactions on Neural Systems and Rehabilitation Engineering, Jun. 2004, vol. 12, No. 2.

Atkeson, C.G., "Learning Arm Kinematics and Dynamics", Annual Reviews, Inc., 1989, vol. 12, pp. 157-183.

Blaya, J., "Force-Controllable Ankle Foot Orthosis (AFO) to Assist Drop Foot Gait," Feb. 2003, web.mit.edu/jblaya/www/MSthesis_final.pdf.

Bronzino, J.D., ed., "The Biomedical Engineering Handbook", IEEE Press, 2nd Ed. vol. 2, 2000, Chapter 142, pp. 1-17.

Flanagan, R.J., et al., "The Role of Internal Models in Motion Planning and Control: Evidence from Grip Force Adjustments During Movements of Hand-Held Loads", The Journal of Neuroscience, Feb. 15, 1997, vol. 17(4), pp. 1519-1528.

Gagnon, D. et al., "The Influence of Dynamic Factors on Triaxial Net Muscular Moments at the L5/S1 Joint During Asymmetrical Lifting and Lowering", Journal of Biomechanics, vol. 25, pp. 891-901, 1992.

Gagnon, M. et al., "Muscular Mechanical Energy Expenditure as a Process for Detecting Potential Risks in Manual Materials Handling," J. Biomech., Nov. 1991, pp. 191-203, vol. 24, No. 3/ 4.

Gruber, K., et al., "A Comparative Study of Impact Dynamics: Wobbling Mass Model Versus Rigid Body Models", Journal of Biomechanics, 31 (1998), pp. 439-444.

Hayashibara, Y. et al., "Design of a Power Assist System with Consideration of Actuator's Maximum Torque," 4th IEEE International Workshop on Robot and Human Communication, RO-MAN'95, Tokyo, Jul. 5-7, 1995, pp. 379-384, [online] Retrieved from the Internet<URL:http://ieeexplore.ieee.org/xpl/abs_free.jsp?arNumber=531990>.

Hemami, H., "A Feedback On-Off Model of Biped Dynamics", IEEE Transactions on Systems, Man, and Cybernetics, Jul. 1980, vol. SMC-10, No. 7, pp. 376-383.

Hsiang, S.H. et al., "Three Different Lifting Strategies for Controlling the Motion Patterns of the External Load", Ergonomics, vol. 40, pp. 928-939, 1997.

Jezernk, S. et al., "Robotic Orthosis Lokomat: A Rehabilitation and Research Tool," Neuromodulation, 2003, pp. 108-115, vol. 6, No. 2.

Kato, H. et al., "The Concept of a Walking Assistance Suit", The Japanese Society of Mechanical Engineers, Aug. 2001.

Kawato, M., "Adapation and Learning in Control of Voluntary Movement by the Central Nervous System", 1989, Advanced Robotics, vol. 3, pp. 229-249.

Kawato, M., et al., "The Cerebellum and VOR/OKR Learning Models", Elsevier Science Publishers Ltd., 1992, vol. 15, No. 11, pp. 445-453.

Park, J.H. et al., Biped Robot Walking Using Gravity-Compensated Inverted Pendulum Mode and Computed Torque Control, 1998 IEEE Conference on Robotics and Automation, May 16-20, 1998, pp. 2528-2533, vol. 4, [online] Retrieved from the Internet<URL:http://ieeexplore.ieee.org/xpl/abs_free.jsp?arNumber=680985>.

Rahman, T. et al., "A Simple Technique to Passively Gravity-Balance Articulated Mechanisms," Journal of Mechanical Design, 1995, pp. 655-658, vol. 117, No. 4.

Shadmehr, R. et al., "Interference in Learning Internal Models of Inverse Dynamics in Humans," Advances in Neural Information Processing Systems, 1995, pp. 1117-1224, Chapter 7.

Shadmehr, R., "Learning Virtual Equilibrium Trajectories for Control of a Robot Arm", Neural Computation, 1990, vol. 2, pp. 436-446.

Transmittal of the International Search Report, PCT/US02/20829, Dec. 12, 2002, 4 pages.

Mihelj, M. et al., "Unsupported Standing with Minimized Ankle Muscle Fatigue," [online] Retrieved from the Internet<URL:http://ieeexplore.ieee.org/iel5/10/29163/01315854.pdf>.

Wells, R. et al., "Internal and Physiological Responses During Concentric and Eccentric Cycle Ergometry," Eur. J. Appl. Physiol., 1986, pp. 291-301, vol. 55.

Winter, D.A., "Biomechanics and Motor Control of Human Movement", 2nd Edition, John Wiley & Sons, Inc., pp. 51-74.

Wolpert, D.M., et al., "Ocular Limit Cycles Induced by Delayed Retinal Feedback", Experimental Brain Research, 1993, vol. 98, pp. 173-180.

Written Opinion, PCT/IB02/04311, Feb. 20, 2003, 2 pages.

Zajac, F.E., "Muscle and Tendon Properties, Models, Scaling, and Application to Biomechanics and Motor Control", 1989, vol. 17, Issue 4, pp. 359-411.

\* cited by examiner

FEEDBACK ESTIMATION OF JOINT FORCES AND JOINT MOVEMENTS

RELATED APPLICATIONS

This application is a continuation of U.S. patent application Ser. No. 10/151,647, entitled "Feedback Estimation of Joint Forces and Joint Movements", that was filed on May 16, 2002 now U.S. Pat. No. 7,135,003 and is incorporated by reference herein in its entirety. U.S. patent application Ser. No. 10/151,647 claims priority, under 35 U.S.C. § 119(e), to U.S. provisional patent application Ser. No. 60/301,891, filed on Jun. 29, 2001, entitled "A recursive, nonlinear feedback approach to estimate joint forces and joint moments from kinesiological measurements," and U.S. provisional patent application Ser. No. 60/353,378, filed on Jan. 31, 2002, entitled "Forward solutions to inverse dynamics problems: a feedback linearization approach," and both of which are incorporated by reference herein in their entireties.

BACKGROUND OF THE INVENTION

1. Field of the Invention

This invention relates to human motion analysis and, more particularly, to analysis of joint forces and moments using nonlinear feedback in a forward dynamic simulation.

2. Description of Background Art

In the study of human motion, inverse dynamics analysis is conventionally used to estimate joint forces and joint moments. In a conventional inverse dynamics analysis, joint forces and joint moments are calculated from the observation of segmental movement. Inverse dynamics analysis is conventionally applied to biomechanics problems because the internal forces of human joints cannot be readily measured. Segmental movements, however, can be measured and joint angles can be inferred from the measured displacement to determine the corresponding joint forces and torques.

A problem with using inverse dynamics in the study of human motion is the error caused by calculating higher order derivatives to determine joint forces and joint moments. Methods for using inverse dynamics concepts in biomechanics are well developed if the input signals are noise-free and the dynamic model is perfect. Experimental observations, however, are imperfect and contaminated by noise. Sources of noise include the measurement device and the joint itself. Inverse dynamics methods for calculating joint moments require the calculation of higher order derivatives of the experimental observations. Specifically, the angular acceleration term is the second derivative of the joint angle and the linear acceleration is the second derivative of the center of mass acceleration. Numerical differentiation of the experimental observations amplifies the noise. The presence of high frequency noise is of considerable importance when considering the problem of calculating velocities and accelerations. The amplitude of each of the harmonics increases with its harmonic number: velocities increase linearly, and accelerations increase proportional to the square of the harmonic number. For example, second order differentiation of a signal with high frequency noise $\omega$ can result in a signal with frequency components of $\omega^2$. The result of this parabolic noise amplification is erroneous joint force and joint moment calculations.

Although techniques exist for filtering the noise, filtering is difficult and time-consuming because much analysis is required to separate the true signal in the biomechanical data from the noise. For example, low-pass filtering is commonly used to reduce high frequency errors. A difficulty in low-pass filtering, however, is the selection of an optimal cutoff frequency $f_c$. Because there is no general solution for selecting optimal filter parameters, filtering techniques often produce unreliable results.

Optimization-based approaches have been proposed to estimate joint forces and joint moments without the errors associated with performing a conventional inverse dynamics analysis. Unlike inverse dynamics, optimization-based methods do not require numerical differentiation. However, the application of optimization-based solutions is limited because the methods are computationally expensive, are not guaranteed to converge, and are generally too complex to implement.

Another problem with using inverse dynamics for analyzing human motion is that the inverse technique lacks the capability to predict the behavior of novel motions. In inverse dynamics, forces and moments are calculated from observed responses. The prediction of novel motions involves calculating the response expected from the application of forces and moments. An inverse dynamics analysis lacks predictive capability because forces and moments are calculated rather than the expected response from the application of those forces and moments.

What is therefore needed is a computationally efficient system and method that: (1) estimates joint forces and joint moments without the errors due to higher order derivatives; (2) does not require closed form, whole body analysis; and (3) is useful for predicting the behavior of human motions.

SUMMARY OF THE INVENTION

One embodiment of the present invention provides an estimation of joint loads in human beings. A joint load includes the forces and moments acting at a joint. A forward dynamics module determines kinematics through numerical integration (or simulation) of the dynamic equations of motion. An error correction controller forces a tracking error between the kinematics obtained from forward simulation and measured (or desired) kinematics to approach zero. The error correction controller generates a modified acceleration for input into an inverse dynamics module. In an embodiment, the modified acceleration represents a value determined without taking the second derivative of the measured (or desired) kinematic data. The estimated joint load, therefore, when applied to the forward dynamics module, tracks the measured (or desired) kinematics without the errors associated with computing higher order derivatives of noisy kinematic data.

In another embodiment, joint loads are recursively estimated for a planar serial link system. In a recursive method, one starts at a first end of a serial chain of segments and calculates joint loads towards a second end of the serial chain. Segments in the chain are connected together by joints and the reaction forces and moments at the joint are shared by the two connected segments. The joint loads estimated for a first segment are used in the estimation for the next segment until the joint or joints in interest are reached. That is, the output of a recursion is a force and moment calculation at the connection point for the next segment. This output is used as an input for the analysis of the next segment. A recursive method, therefore, does not require modeling the dynamics of the whole body. Although in a particular case it may be desirable to model recursively whole body dynamics, the recursive method provides flexibility that can reduce sources of error.

Recursive embodiments include open chain estimations and closed chain estimations. An open chain system is constrained with the environment at one end, and the remaining terminal segments are free. A closed chain system has more than one end in contact with the environment. The segments of the link system are numbered in order of recursion beginning with segment 1 toward segment n, which is the last segment of interest. Segment n is not necessarily the last segment in the multi-body system. Rather segment n is denoted the segment at which it is desired to stop the recursive computation such that the forces and moments of interest are found. In order to initiate the recursion, one requires the force and moment acting at the first segment. For example, in human motion analysis, the ground reaction forces under the feet are typically measured and initiate the recursion equations. The use of the ground reaction forces improves the precision of joint load estimates at the joints in proximity to the ground.

In a further embodiment, the tracking system of the present invention can be applied to closed form dynamics. The closed form system equations for an unconstrained rigid body system are described by n differential equations. Similar to the recursive embodiments described herein, a control law is used to linearize and to decouple the system dynamics.

Further features of the invention, its nature and various advantages will be more apparent from the accompanying drawings and the following detailed description.

BRIEF DESCRIPTION OF THE DRAWINGS

The accompanying drawings, which are incorporated in and constitute a part of this specification, illustrate several embodiments in accordance with the present invention and, together with the description, serve to explain the principles of the invention.

DETAILED DESCRIPTION OF THE PREFERRED EMBODIMENTS

Preferred embodiments of the present invention are now described with reference to the accompanying figures where like reference numbers indicate identical or functionally similar elements. Also in the figures, the left most digit of each reference number corresponds to the figure in which the reference number is first used.

Figure 1:
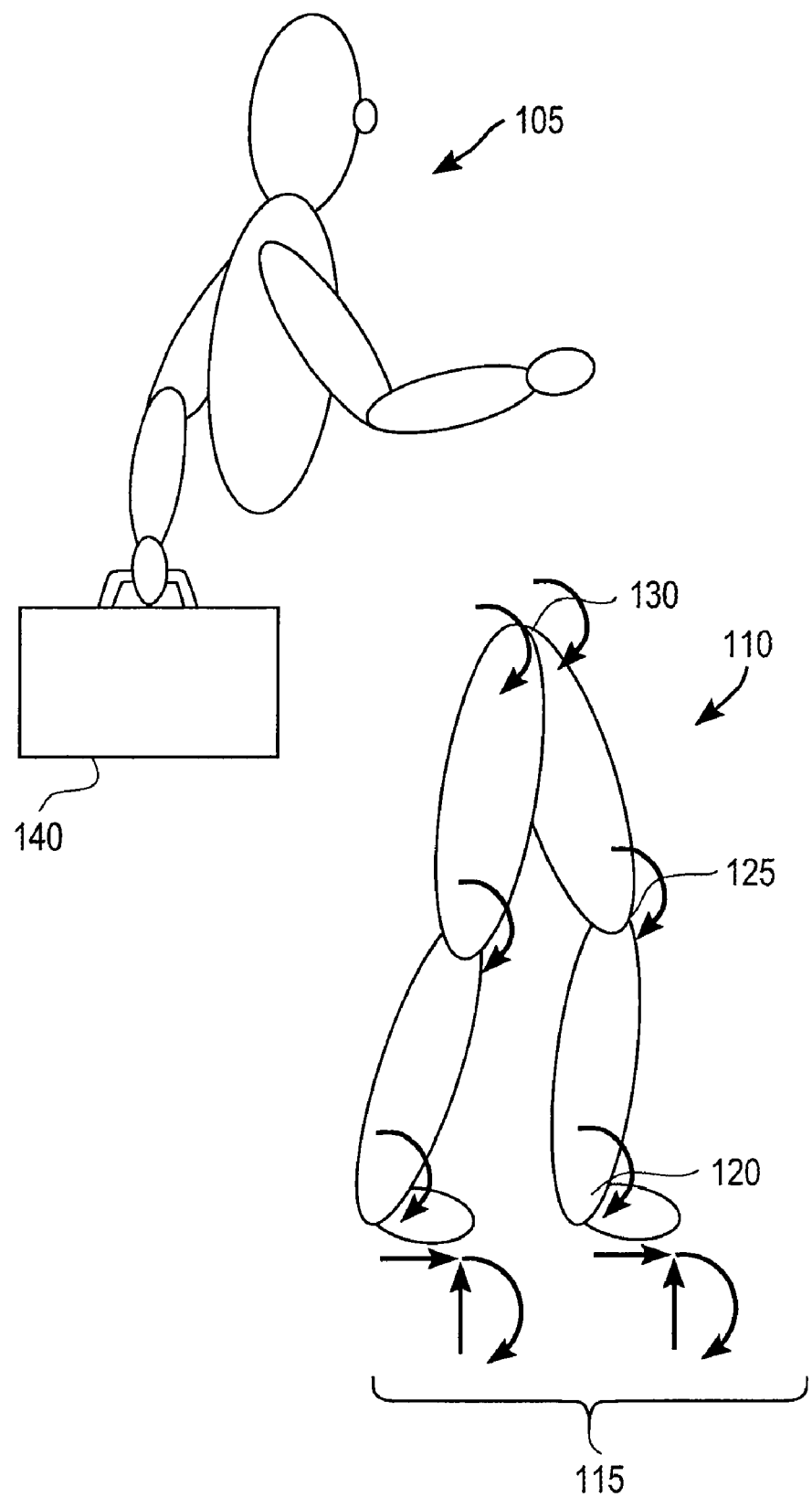
FIG. 1 is an illustration of how a recursive calculation can be used to separate lower body dynamics from upper body dynamics.

FIG. 1 is an illustration showing how recursive calculation is used to separate lower body dynamics from upper body dynamics. The illustration includes upper body portion 105 and lower body portion 110. A segment of upper body portion 105 is illustrated with load 140. Lower body portion 110 includes segments having ankle joint 120, knee joint 125, and hip joint 130. In a recursive method for computing joint forces and moments, the upper body portion 105 can be modeled separately from the lower body portion 110. Starting with ground reaction forces 115, one can effectively isolate joints 120, 125, and 130 of lower body portion 110 as well as the associated link segment parameters, from upper body portion 105. That is, the internal forces and moments acting on joints 120, 125, and 130 can be estimated without considering the effects due to load 140 or the physical parameters of upper body portion 105, such as mass, center of mass, inertia, and segment length. These parametric uncertainties in upper body portion 105 are significant sources of error in the estimation of the internal forces and moments in the human body when using closed form, whole body dynamic procedures. In contrast to a closed form whole body solution, embodiments of a recursive solution use measurements of ground reaction forces 115 as constraints to compute recursively the joint moments from the ground and working up toward the, e.g., knee joint 125 and hip joint 130.

An advantage of using a recursive method to estimate joint forces and moments is the ability to focus on joints of interest without introducing additional sources of error. Further, a recursive method with measurements of ground reaction forces 115 as input, for example, provides an extra sensing modality. That is, combining kinematic and reaction force information provides an additional cue that increases the reliability of the resulting internal force estimations. Human beings may be subjected to unpredictable loads, or constrained dynamics resulting from interaction with other objects or other people in the environment. Such circumstances can alter the dynamic representation required to estimate the internal forces and moments at the joints. Some applications for using a recursive method in these circumstances include performing biomechanical studies of lifting tasks and developing controls for assistive devices that aid the physically impaired in everyday tasks. One skilled in the art will appreciate that in-shoe force and pressure sensing devices are complementary technologies that can be used to provide extra sensing modalities for use in various force and moment estimations.

Recursive Method for a Two-Dimensional Serial Chain System

Embodiments of the present invention are applicable to planar systems including recursive open chain and recursive closed chain. In an open chain system, at most one end of the multi-body system is in contact with the environment. The other end or ends are free or unconstrained. In a closed chain system, more than one end is in contact with the environment.

Figure 2:
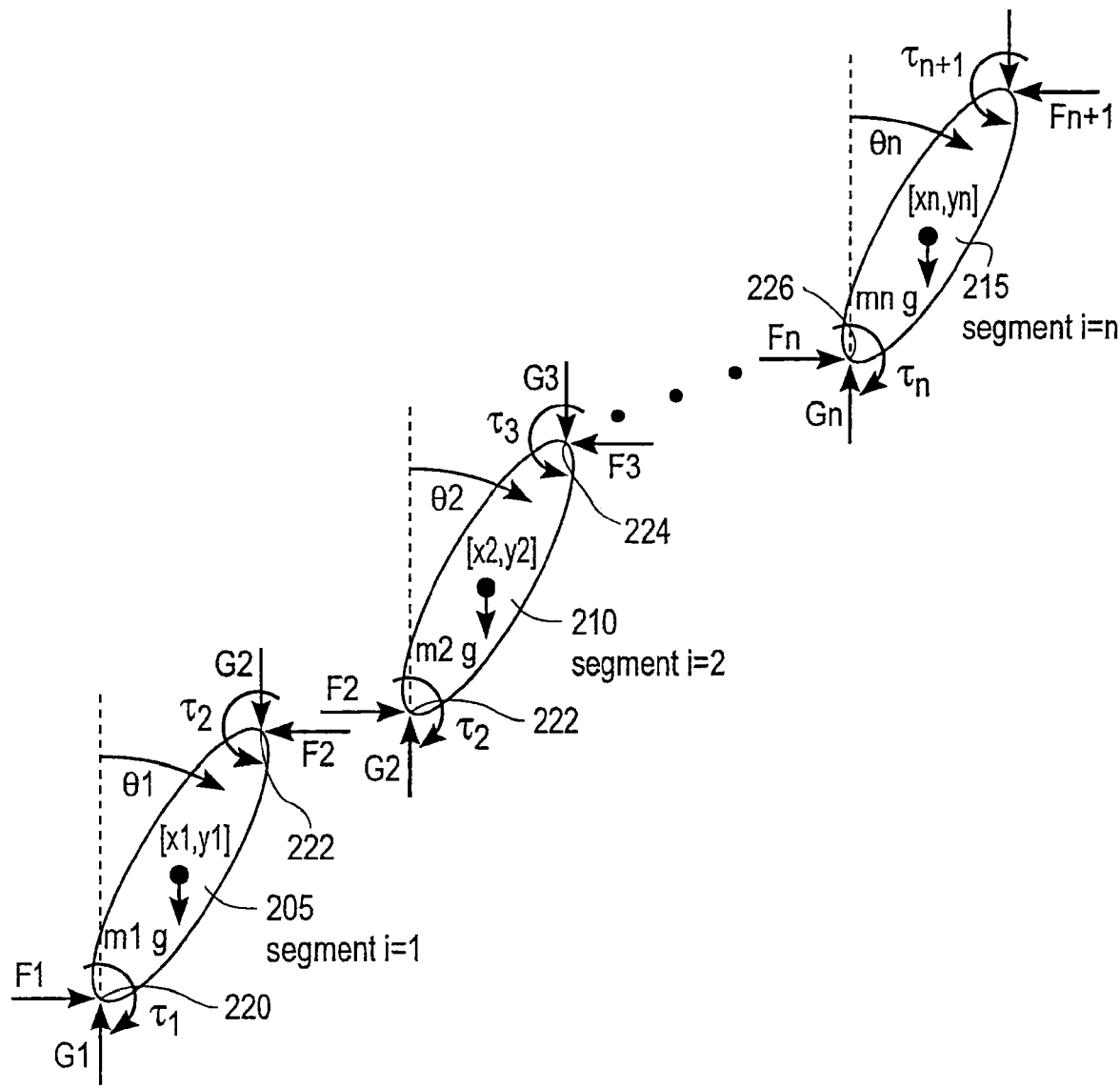
FIG. 2 is a free body diagram of forces acting on segments in an open chain, planar serial link system.

FIG. 2 is a free body diagram of forces acting on segments in an open chain, planar serial link system. The system includes first segment 205, second segment 210, and $n^{th}$ segment 215. The segments 205, 210, and 215 are linked by revolute joints. Each of segments 205, 210, and 215 is illustrated as a free body diagram in which first joint 220, second joint 222, third joint 224, and $n^{th}$ joint 226 connect the segments. First segment 205 includes first joint 220 and second joint 222. Second segment 210 includes second joint 222 and third joint 224. In particular, segments 205 and 210 are connected as follows: second joint 222 links first segment 205 with second segment 210. Therefore, a serial chain of n segments is formed by connecting the n segments at the common or overlapping joint.

For each of joints 220, 222, 224, and 226, the joint torques, the horizontal reaction forces, and the vertical reaction forces at each joint is illustrated and denoted by $\tau_i$, $F_i$, and $G_i$ respectively. For example, with respect to first joint 220, the joint torque $\tau_1$, horizontal reaction force $F_1$, and vertical reaction force $G_1$ are illustrated. With reference to FIG. 2, an instance of a recursive calculation is now described. In a recursive calculation, a multi-body system is conceptually separated into individual segments. The free body diagram of each segment is analyzed. The segments are connected together by joints, e.g., second joint 222. The reaction forces and moments at, e.g., second joint 222 are shared by first segment 205 and second segment 210. Analysis begins at first segment 205, where the force and moment at the connection point of the second segment 210, i.e., second joint 222 are computed. The calculated forces and moment at second joint 222 are the output of recursion 1. This output is used as input for the analysis of the next segment, e.g., second segment 210. The recursive analysis of segments continues until $n^{th}$ segment 215 is reached. The $n^{th}$ segment 215 is the segment of interest or the segment at which it is desired to stop the recursive computation. In an embodiment where ground reaction forces 115 (FIG. 1) are acting on first segment 205, one computes the forces and moment acting on second joint 222 in terms of the forces and moment acting on first joint 220. Next, one computes the forces and moment acting on third joint 224 in terms of the previously computed forces and moment acting on second joint 222. This recursive procedure of using the output of dynamics calculations as input for the next calculation is repeated until forces and moments have been found for the joint or joints in interest. One skilled in the art will appreciate that $n^{th}$ segment 215 is not necessarily the last segment in the multi-body system. Rather, $n^{th}$ segment 215 is denoted the segment at which it is desired to stop the recursive computation such that the forces and moments of interest are found. It should further be noted that ground reaction forces 115 act at the point of contact, which is not necessarily at the joint. Further details of the calculations are described below and with respect to FIG. 3.

Figure 3:
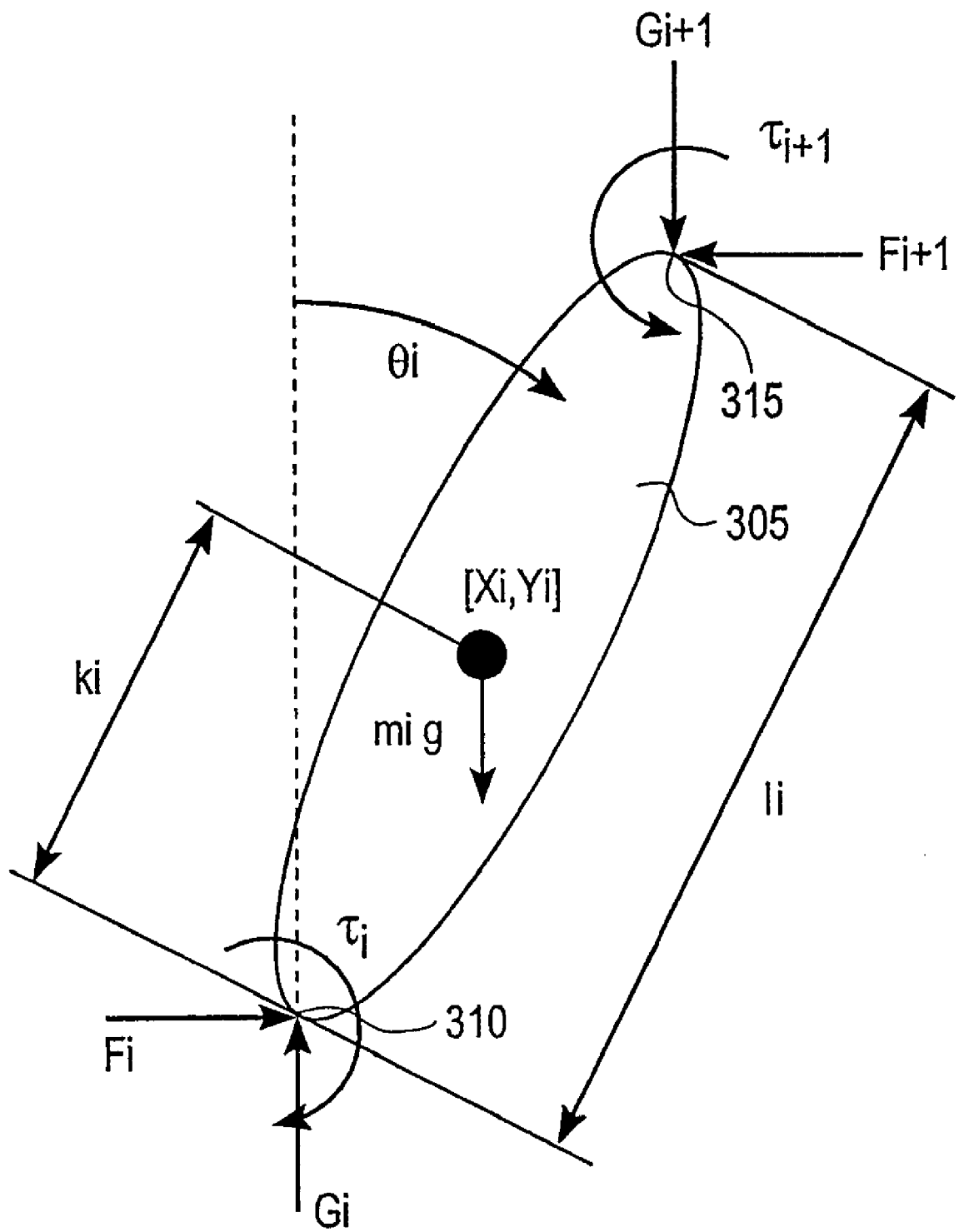
FIG. 3 is a free body diagram of one segment within the serial link system.

FIG. 3 is a free body diagram of one segment within the serial link system. Body segment 305 represents the $i^{th}$ segment of a planar serial link system, such as the system illustrated in FIG. 2. Body segment i includes joint i (310) and joint i+1 (315). For isolated body segment i, where i=1 . . . n, the acceleration of the center of mass is $(\ddot{x}_i, \ddot{y}_i)$, the joint angle with respect to the vertical is $\theta_i$, and the angular acceleration is $\ddot{\theta}_i$. As illustrated in FIG. 3, the physical parameters for body segment i are mass $m_i$, moment of inertia $I_i$, segment length $l_i$, and length to center of mass $k_i$. Also illustrated in FIG. 3 for each of joints 310 and 315 are joint torques $\tau_i$, horizontal reaction forces $F_i$, and vertical reaction forces $G_i$. The Newton-Euler equations for computing the forces and moments at each of joints 310 and 315 of body segment i are set forth below as Equation 1, Equation 2, and Equation 3.

$$m_i \ddot{x}_i = F_i - F_{i+1} \tag{1}$$

$$m_i \ddot{y}_i = G_i - G_{i+1} - m_i g \tag{2}$$

$$I_i \ddot{\theta}_i = -F_i k_i \cos(\theta_i) + G_i k_i \sin(\theta_i) - F_{i+1}(l_i - k_i)\cos(\theta_i) + G_{i+1}(l_i - k_i)\sin(\theta_i) + \tau_i - \tau_{i+1} \tag{3}$$

One skilled in the art will appreciate that Equation 1 represents an expression for summing the forces acting on body segment 305 in the x or horizontal direction. Similarly, Equation 2 represents an expression for summing the forces acting on body segment 305 in the y or vertical direction. In Equation 2, the gravitational acceleration is represented by g. Equation 3 represents an expression for summing the angular accelerations acting at joints 310 and 315.

Inverse Dynamics Methodology

In inverse dynamics analysis, the forces and moments acting at the joints are computed from measured or desired kinematic data. Kinematic data includes center of mass coordinates and joint angle data. In an embodiment of the present invention, a recursive solution to compute the forces and moments at each joint can be obtained from a compact representation (matrix form) of the Newton-Euler equations as set forth in Equation 4 below. In Equation 4, $U_i = [F_i \; G_i \; \tau_i]^T$ is a vector (transposed) whose elements correspond to the horizontal force, vertical force, and moment acting at joint i (310), respectively. The forces and moment at joint i+1 (315) are described by $U_{i+1}$. Further details of a recursive solution for $U_i$ or $U_{i+1}$ are described below.

$$M_i \ddot{q}_i = A_i U_{i+1} + B_i U_i + P_i \tag{4}$$

Vector $q_i=[x_i\ y_i\ \theta_i]^T$ represents the center of mass coordinates and joint angle at joint i. One skilled in the art will appreciate that the term $\ddot{q}_i$ in Equation 4 represents the second derivative of vector $q_i$. The elements of Equation 4 are defined in additional detail as follows:

$$M_i = \begin{bmatrix} m_i & 0 & 0 \\ 0 & m_i & 0 \\ 0 & 0 & I_i \end{bmatrix} \ddot{q}_i = \begin{bmatrix} \ddot{x}_i \\ \ddot{y}_i \\ \ddot{\theta}_i \end{bmatrix} P_i = \begin{bmatrix} 0 \\ -m_i \\ 0 \end{bmatrix} g$$

$$A_i = \begin{bmatrix} -1 & 0 & 0 \\ 0 & -1 & 0 \\ -(l_i - k_i)\cos(\theta_i) & (l_i - k_i)\sin(\theta_i) & -1 \end{bmatrix} U_{i+1} = \begin{bmatrix} F_{i+1} \\ G_{i+1} \\ \tau_{i+1} \end{bmatrix}$$

$$B_i = \begin{bmatrix} 1 & 0 & 0 \\ 0 & 1 & 0 \\ -k_i\cos(\theta_i) & k_i\sin(\theta_i) & 1 \end{bmatrix} U_i = \begin{bmatrix} F_i \\ G_i \\ \tau_i \end{bmatrix}$$

Open Chain Estimation

As described above, an open chain system has one end in contact with the environment. The one end in contact with the environment is termed a constrained end. In an embodiment of the present invention, the constrained end is a human being's feet that are in contact with the ground or other supporting surface. In one embodiment, kinematic data is supplemented with measurements of ground reaction forces 115 (denoted $U_1$) to improve the precision of the internal force and moment estimations. The segments are numbered from the "ground up" from 1 to n, with n being the last segment of interest. Thus the Newton-Euler inverse dynamics methodology makes use of measurements of the forces and moments under the feet. With $U_1$ available as a boundary condition at segment 1, the force and moment at segment i, where i has a value from 1 to n (i:1→n) is computed successively with Equation 5, starting with segment 1 and working toward segment n. In an open chain estimation and with n being the last segment in the chain, there are no external forces applied at segment n, such that $U_{n+1}=0$.

$$U_{i+1}=A_i^{-1}[M_i\ddot{q}_i-B_iU_i-P_i] \quad (5)$$

Due to noisy measurements and errors in the biomechanical model, the boundary condition at the segment that is free is generally violated. In other words, in an open chain embodiment whereby the recursion proceeds from segment 1 to the free segment (denoted by n), then $U_{n+1}$ is not equal to 0. The over-determinacy is resolved by adding residual forces and torques to segment n. An advantage of a recursive formulation, numbering the segments from 1 to n, is that the entire body need not be modeled. The force and moment estimation is complete at segment n regardless of whether segment n is the last segment of the serial system. The parametric uncertainties in the upper extremities and uncertainties in the rigid-body model are significant sources of error in the estimation of the internal forces and moments. These uncertainties in the upper extremities can be avoided, however, when only joint moments proximal to the force plate are desired.

In another open chain embodiment, only kinematic measurements are available. The segments are labeled from 1 to n, wherein segment 1 has a free end, rather than a constrained end. Because segment 1 has a free end, $U_1=0$ is available as a boundary condition for the recursion to segment n.

Closed Chain Estimation

In another embodiment of the present invention, closed chain estimation is performed. As described above, a closed chain system has more than one end in contact with the environment. In this embodiment, sensor measurements or other initial forces are needed to estimate the internal forces and moments. The segments are serially numbered beginning with segment 1 toward segment n, which is the last segment of interest. The sensor measurement or initial force at segment 1 is denoted $U_1$, wherein $U_1 \neq 0$ because the end of segment 1 is constrained. With measurements for $U_1$ available as a boundary condition at segment 1, the force and moment at segment i, where i has a value from 1 to n (i:1→n) is computed successively with Equation 5, starting with segment 1 and working toward segment n.

Inverse Solution Using Nonlinear Feedback

Figure 4:
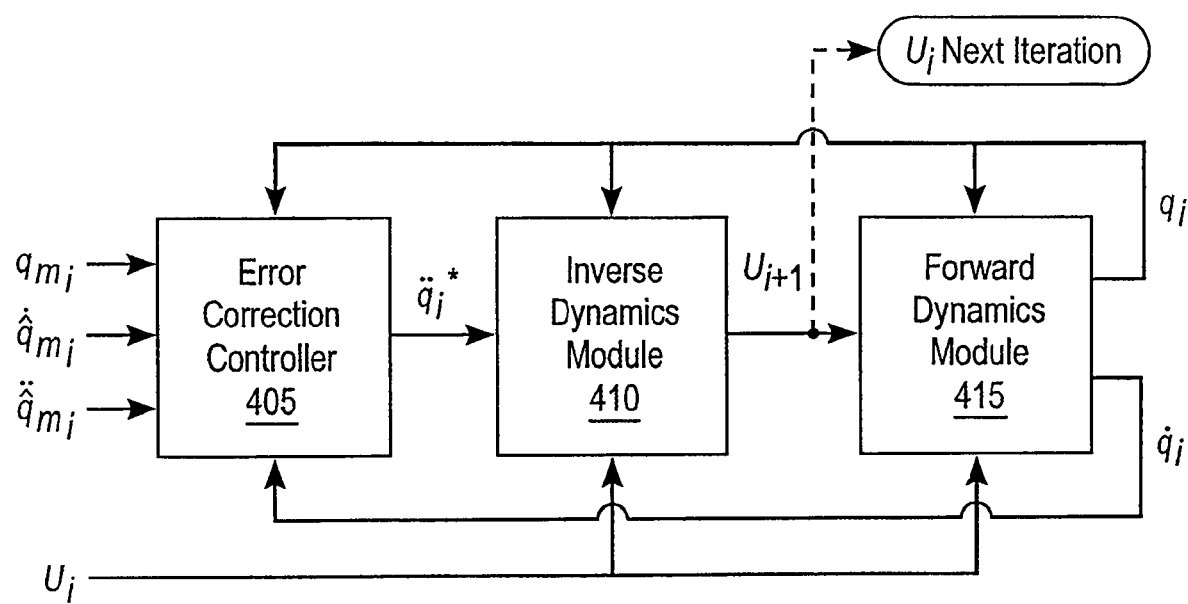
FIG. 4 is a block diagram of a tracking system for link segment i.

FIG. 4 is a block diagram of a tracking system for body segment i. Error correction controller 405, inverse dynamics module 410, and forward dynamics module 415 are coupled to form a tracking system. Inputs to error correction controller 405 include kinematic data $q_{m_i}$, $\dot{q}_{m_i}$, and $\ddot{q}_{m_i}$, as well as state variables $q_i$ and $\dot{q}_i$. In an embodiment, the measured or desired kinematics ($q_{m_i}$) and estimates of their velocities ($\dot{q}_{m_i}$) are required. The estimated accelerations ($\ddot{q}_{m_i}$) can be used in noise free applications, but are not required. Error correction controller 405 outputs a modified acceleration $\ddot{q}_i^*$ as an input to inverse dynamics module 410. Inverse dynamics module 410 has additional inputs of $U_i$ and $q_i$. The vector $U_i$ represents the forces and moment at joint i. The output of inverse dynamics module 410 is force and moment estimates $U_{i+1}$ for joint i+1. Inputs to forward dynamics module 415 include $U_i$, $U_{i+1}$, and $q_i$. Additionally, the estimated joint force and moment $U_{i+1}$ is used as input during the next iteration, where it is referred to as $U_i$ for an incremented i. In each iteration or recursive instance, $U_i$ is input and $U_{i+1}$ is output. Forward dynamics module 415 outputs state variables $q_i$ and $\dot{q}_i$. The parameters for the forward dynamics module (i.e., $A_i$, $M_i$, $B_i$, and $P_i$) are identical to the inverse dynamics parameters.

In an embodiment, joint forces and moments are estimated using inverse dynamics module 410. Equation 6 represents an inverse dynamics control law for recursively calculating joint load information for $U_{i+1}$ using modified acceleration $\ddot{q}_i^*$. Forward dynamics module 415 computes the accelerations as in Equation 7 and subsequently numerically integrates the accelerations to obtain the state variables $q_i$ and $\dot{q}_i$ associated with joint i. Error correction controller 405 uses feedback of state variables $q_i$ and $\dot{q}_i$ to generate the modified acceleration $\ddot{q}_i^*$. In an embodiment, modified acceleration $\ddot{q}_i^*$ represents a value computed without taking the second derivative of measured or desired kinematic data. Error correction controller 405 generates the modified acceleration term $\ddot{q}_i^*$ such that inverse dynamics module 410 computes a set of inputs or controls denoted by $U_{i+1}$ that when applied to forward dynamics module 415 substantially reproduces or tracks the measured or desired kinematic data $q_{m_i}$.

$$U_{i+1}=A_i^{-1}[M_i\ddot{q}_i^*-B_iU_i-P_i] \quad (6)$$

The forward dynamics module 415 performs a simulation to find state variables $q_i$ and $\dot{q}_i$ based on the calculated forces and moment. Specifically, forward dynamics module 415 numerically integrates Equation 7 to find the position and velocity vectors that correspond to the applied joint load information $U_{i+1}$. In one embodiment, numerical integration is performed by an integration function in MATLAB software that is commercially available from The MathWorks, Inc., Natick, Mass. One skilled in the art will appreciate that integration can be performed by many methods, e.g., Runge Kutta methods. The state variables $q_i$ and $\dot{q}_i$ are input to error correction controller 405, which computes modified acceleration $\ddot{q}_i^*$ for the current time step. Starting with initial conditions $q_i(0)$ and continuing to an endpoint, error correction controller 405 forces the tracking error between the simulated and measured (or desired) kinematics to approach zero.

$$\ddot{q}_i = M_i^{-1}[A_i U_{i+1} + B_i U_i + P_i] \quad (7)$$

One skilled in the art will appreciate that the described equations, expressions, modules, or functions can be implemented in a general-purpose computer, special purpose computer, or hardware. In an embodiment, a software programmable general-purpose computer implements features of the invention. The software is preferably distributed on a computer readable medium, which includes program instructions. A computer readable medium includes, for example, a computer readable storage volume. The computer readable storage volume can be available via a public computer network, a private computer network, or the Internet. One skilled in the art will appreciate that the program instructions can be in any appropriate form, such as source code, object code, or scripting code.

Figure 5:
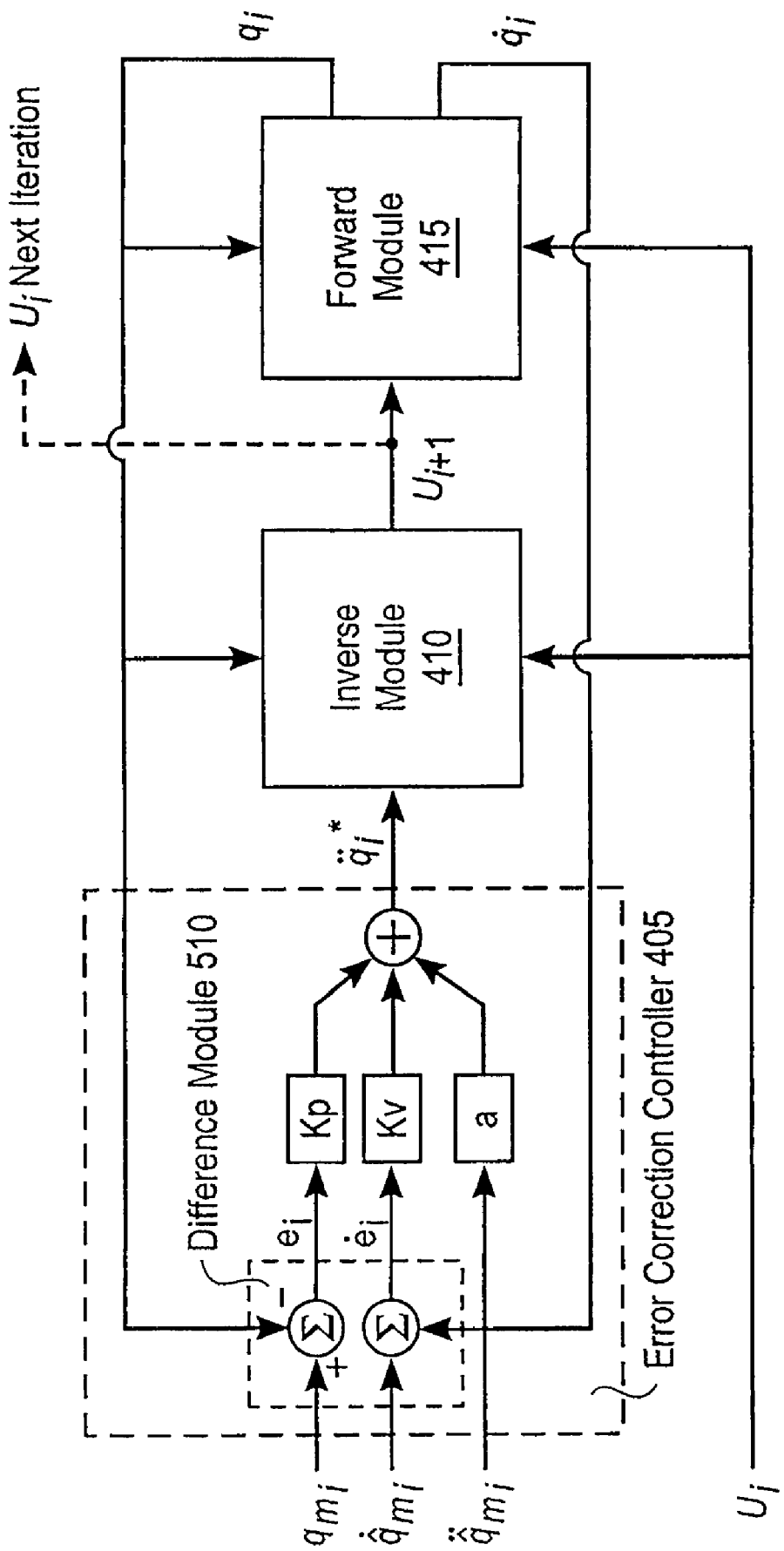
FIG. 5 is a block diagram of a tracking system for link segment i illustrating further details of an error correction controller.

FIG. 5 is a block diagram of a tracking system for body segment i illustrating further details of an error correction controller. In the illustrated embodiment, error correction controller 405 comprises modules that implement Equation 8, where parameter $K_{p_i}$ represents the positional feedback gain and parameter $K_{v_i}$ represents the velocity feedback gain. A difference module 510 is configured to generate an error value $e_i$ (defined in Equation 12) and a derivative error value $\dot{e}_i$ from the kinematics obtained from simulation and measured (or desired) kinematics. In the error correction controller 405, error value $e_i$ is multiplied by positional feedback gain $K_{p_i}$ and the derivative error value $\dot{e}_i$ is multiplied by velocity feedback gain $K_{v_i}$ to generate modified acceleration $\ddot{q}_i^*$. Parameters $K_{p_i}$ and $K_{v_i}$ are defined in Equations 9 and 10 as constant diagonal matrices that control Equations 1, 2, and 3.

$$\ddot{q}_i^* = a\ddot{q}_{m_i} + K_{v_i}(\dot{q}_{m_i} - \dot{q}_i) + K_{p_i}(q_{m_i} - q_i). \quad (8)$$

$$K_{p_i} = \begin{bmatrix} k_{p_x} & 0 & 0 \\ 0 & k_{p_y} & 0 \\ 0 & 0 & k_{p_\theta} \end{bmatrix} \quad (9)$$

$$K_{v_i} = \begin{bmatrix} k_{v_x} & 0 & 0 \\ 0 & k_{v_y} & 0 \\ 0 & 0 & k_{v_\theta} \end{bmatrix} \quad (10)$$

The parameter a is included to study the effect of including accelerations (a=1) and excluding accelerations (a=0) during the simulation. One skilled in the art will appreciate that when parameter a is set equal to zero the second derivative of the kinematic data, the estimated accelerations term $\ddot{q}_{m_i}$, is ignored in Equation 8. Therefore, in such a case, only modified acceleration $\ddot{q}_i8$ is used in the tracking system. An advantage of not using the second derivative of noisy kinematic data is improved accuracy of force and moment estimation.

Figure 6:
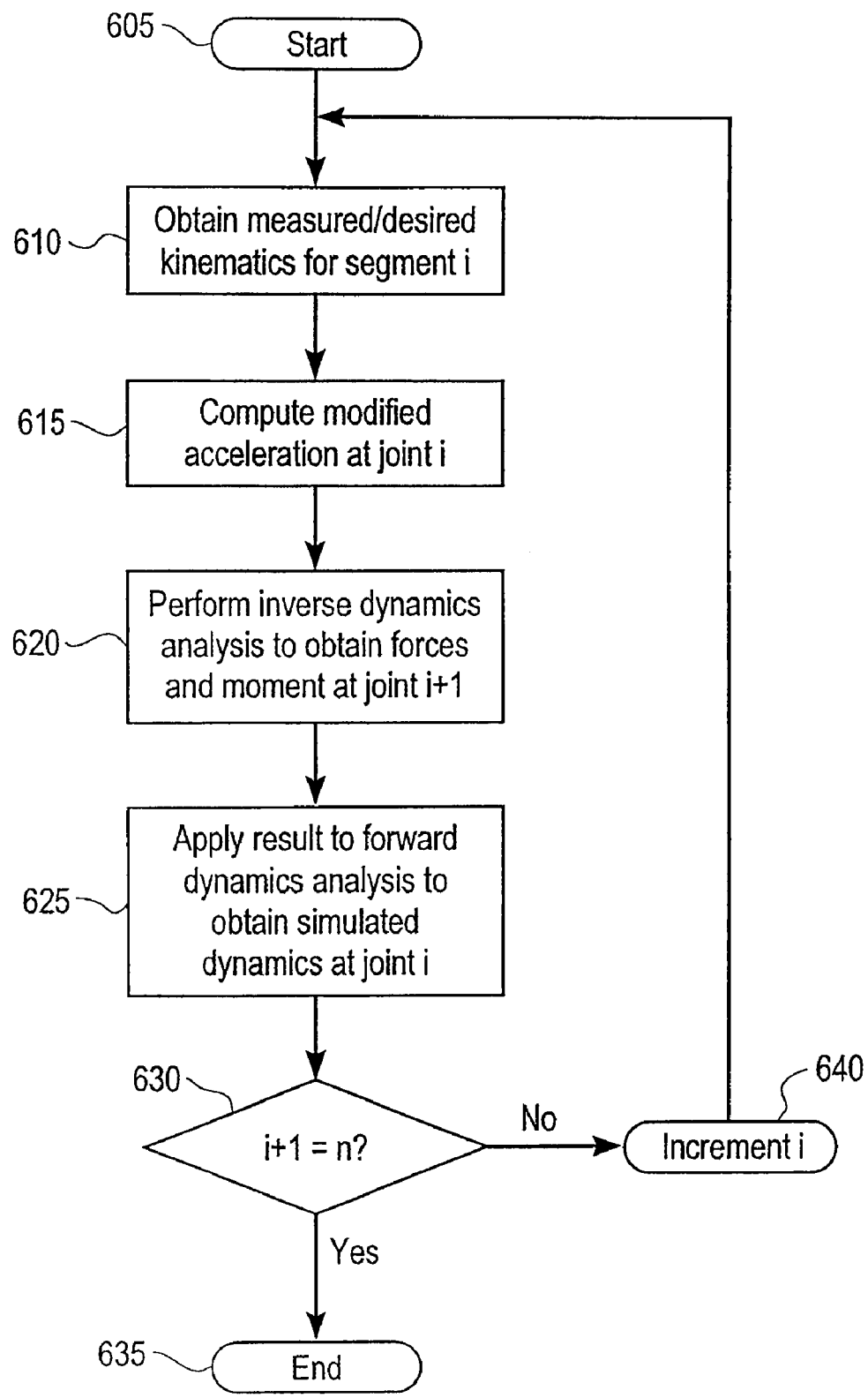
FIG. 6 is a flowchart illustrating a recursive tracking process.

FIG. 6 is a flowchart illustrating a recursive tracking process. The initial value of i is 1 for a serial link system with n segments of interest. As described above, n represents the last segment of interest, i.e., the stopping point for the recursion. The process begins with step 605. Measured or desired kinematics are obtained 610 for segment i. As described above, segment i has joints labeled i and i+1. Next, modified acceleration $\ddot{q}_i^*$ is computed 615 at joint i using an embodiment of the feedback structure described above. An inverse dynamics analysis is performed 620 to obtain forces and moment at joint i+1. In the recursion instance where i=1, reaction force/moment at joint 1 provides input into step 620 as $U_1$. In other recursion instances where i≠1 and i+1<n, the joint load information for joint i+1 (represented as concatenated vector $U_{i+1}$) is applied as input $U_i$ for the next body segment in another recursion instance. $U_{i+1}$ is applied 625 to a forward dynamics analysis to obtain the simulated kinematic data at joint i. The process determines 630 whether additional recursion is needed. If i+1 is equal to n then control proceeds to step 635 where the recursion ends, otherwise the value of i is incremented by 1 in step 640 and control returns to step 605 where another recursion instance performs the tracking process for the next body segment.

Forward Prediction of Novel Motions

In an embodiment of the present invention, the simulation of the dynamic equation of motion, produced by the forward dynamics module, can be used to predict novel movements. The simulated kinematic data represents segmental position and velocity data from the estimated joint load (including forces and moments). The forward dynamics module, therefore, can be configured to simulate novel movements of body segments in response to applied forces and moments.

Various parameters in the forward model can be altered and the effects on the simulated response can be observed. For example, changing segment parameters such as mass, inertia, length, and center of mass in forward dynamics module 415 effects the kinematic response. This type of predictive capability enables study of the sensitivity of forward dynamics module 415 to the physical parameters.

Error Dynamics

The joint torque and force estimation problem is described herein in an embodiment as a tracking system using a nonlinear feedback control law described by Equation 6. To demonstrate the tracking performance, it is instructive to consider the closed loop error dynamics. With reference to FIG. 5, the output of the inverse dynamics module $U_{i+1}$, represents the control law of Equation 6. If this control law is applied to the forward dynamics module (by substitution in Equation 4), the closed loop relation of Equation 11 is obtained. Equation 12 defines $e_i$ as the error between the measured kinematics $q_{m_i}$ and the simulated state variable $q_i$, which is obtained by integration in the forward dynamics module 415. The error dynamics for several scenarios are described below.

$$a\ddot{q}_{m_i} - \ddot{q}_i + K_{v_i}(\dot{q}_{m_i} - \dot{q}_i) + K_{p_i}(q_{m_i} - q_i) = 0 \quad (11)$$

$$e_i = q_{m_i} - q_i \quad (12)$$

Accelerations Included: a=1

In an ideal situation of perfect measurements and zero error in numerical differentiation, the closed loop error dynamics are defined in differential Equation 13.

$$\ddot{e}_i + K_{v_i} \dot{e}_i + K_{p_i} = 0 \quad (13)$$

The error dynamics of state variable $q_i$ can be independently controlled by eigenvalue assignment. Let $\lambda_1$ and $\lambda_2$ denote the eigenvalues of the Equation 13. Equation 14 provides a critically damped solution, i.e., no sinusoidal oscillations, with real and equal eigenvalues. This solution yields the fastest non-oscillatory response.

$$e(t)=c_1 e^{\lambda_1 t}+c_2 t e^{\lambda_2 t} \tag{14}$$

The relationship between $K_p$ and $K_v$ to achieve a critically damped response is set forth in Equation 15.

$$K_v = 2\sqrt{K_p} \tag{15}$$

In an embodiment, proper tracking and calculation time can be achieved with eigenvalues having a value of 100. Simulation results with both small and large feedback gains are described below and with respect to FIGS. 8-23.

Accelerations Ignored: a=0

Suppose the accelerations estimated from the measured kinematics are ignored by setting a=0. The closed loop error dynamics are expressed by non-homogeneous differential Equation 16.

$$\ddot{e}_i + K_{v_i}\dot{e}_i + K_{p_i} = \ddot{q}_{m_i} \tag{16}$$

Although the solution to Equation 16 contains a forcing term, assuming the acceleration term $\ddot{q}_{m_i}$ is bounded, the error converges to zero by assigning the eigenvalues of Equation 16 to have negative and real parts. As before where accelerations were included, the feedback gains can be appropriately designed for a critically damped response using the relation given in Equation 15.

Incorporating Derivative Estimation Error

In the above formulation of the error equations, it is assumed that the derivative term $\dot{q}_{m_i}$ and acceleration term $\ddot{q}_{m_i}$ can be precisely calculated by differentiating the kinematic data. Indeed, errors in numerical differentiation of noisy kinematic measurements cannot be ignored and are considered in the following formulation.

Let $\epsilon_v$ and $\epsilon_a$ represent the bounded error in the velocity and acceleration computations. The estimates $$\hat{\dot{q}}_{m_i} \text{ and } \hat{\ddot{q}}_{m_i}$$

are expressed as follows in Equation 17:

$$\hat{\dot{q}}_{m_i} = \dot{q}_{m_i} + \varepsilon_v \tag{17}$$

$$\hat{\ddot{q}}_{m_i} = \ddot{q}_{m_i} + \varepsilon_a$$

The closed loop dynamics incorporating the derivative estimation error is given by Equation 18.

$$a\hat{\ddot{q}}_{m_i} - \ddot{q}_i + K_{v_i}(\hat{\dot{q}}_{m_i} - \dot{q}_i) + K_{p_i}(q_{m_i} - q_i) = 0 \tag{18}$$

Substituting Equation 17 into Equation 18, the following Equation 19 is derived.

$$a\ddot{q}_{m_i} - \ddot{q}_i + K_{v_i}(\dot{q}_{m_i} - \dot{q}_i) + K_{p_i}(q_{m_i} - q_i) = -(a\epsilon_a + K_{v_i}\epsilon_v) \tag{19}$$

The error dynamics for a=0 and a=1 are given by Equations 20 and 21.

$$\ddot{e}_i + K_{v_i}\dot{e}_i + K_{p_i} = -K_{v_i}\epsilon_v + \ddot{q}_{m_i} \quad a=0 \tag{20}$$

$$\ddot{e}_i + K_{v_i}\dot{e}_i + K_{p_i} = -(\epsilon_a + K_{v_i}\epsilon_v) \quad a=1 \tag{21}$$

Closed Form System Dynamics

In a further embodiment, the tracking system can be applied to closed form dynamics. The closed form system equations for an unconstrained rigid body system are described by n differential equations in the matrix form of Equation 22. In Equation 22, M corresponds to the mass matrix, and P corresponds to the contributions due to the coriolis, centrifugal, and gravity terms, respectively. The inputs U correspond to the net joint torques. Similar to the recursive embodiments described herein, the control law of Equation 23 is used to linearize and to decouple the system dynamics. The $\ddot{q}^*$ term of Equation 23 is defined in Equation 24, wherein $K_p$ and $K_v$ are n×n diagonal matrices configured to have a critically damped response.

$$M\ddot{q}=U+P \tag{22}$$

$$U=M\ddot{q}^*-P \tag{23}$$

$$\ddot{q}^* = a\ddot{q}_m + K_v(\dot{q}_m - \dot{q}) + K_p(q_m - q) \tag{24}$$

Simulation of Open Chain Planar System

Figure 7:
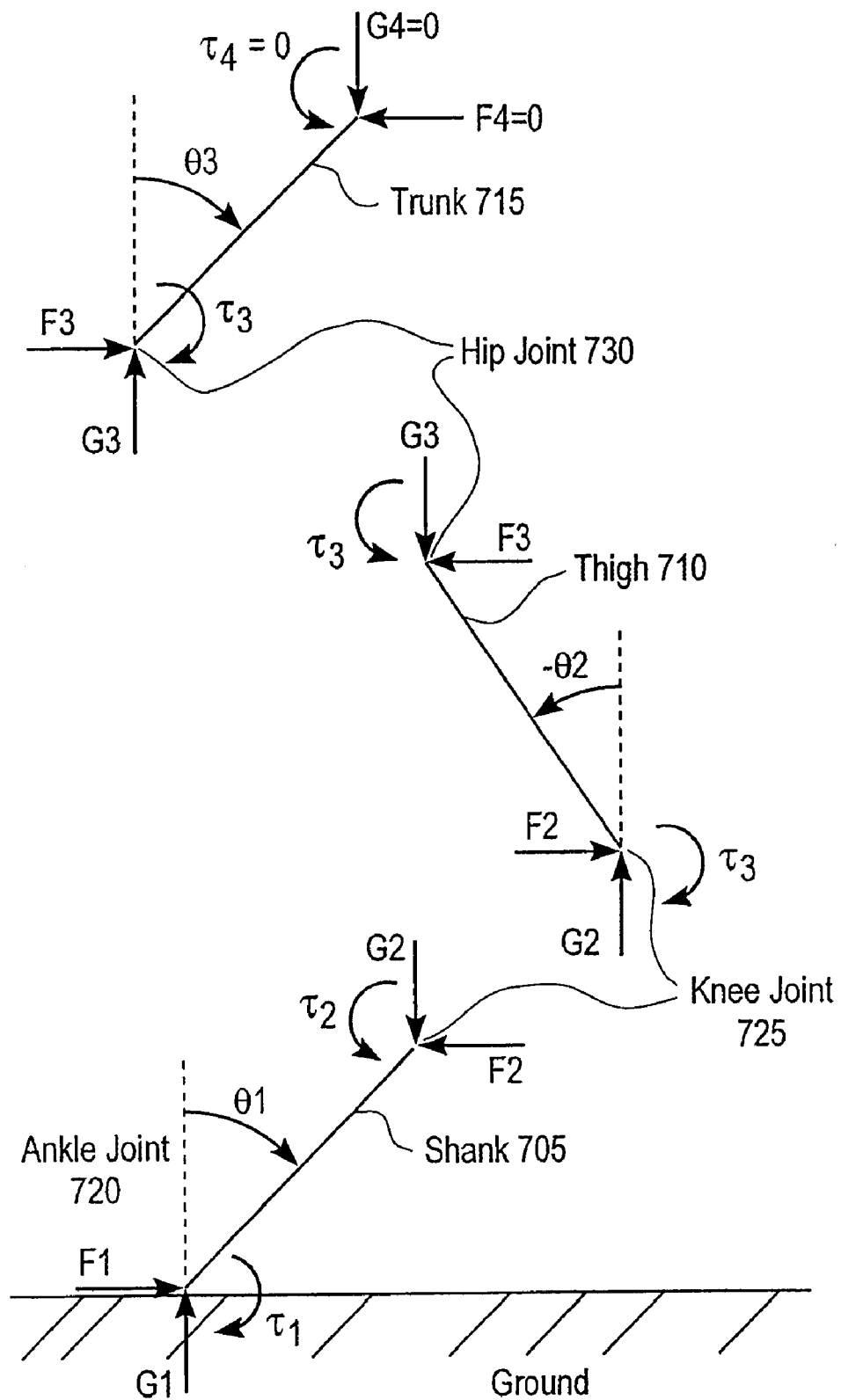
FIG. 7 is a free body diagram illustrating a three segment, two-dimensional system.
Figure 8A:
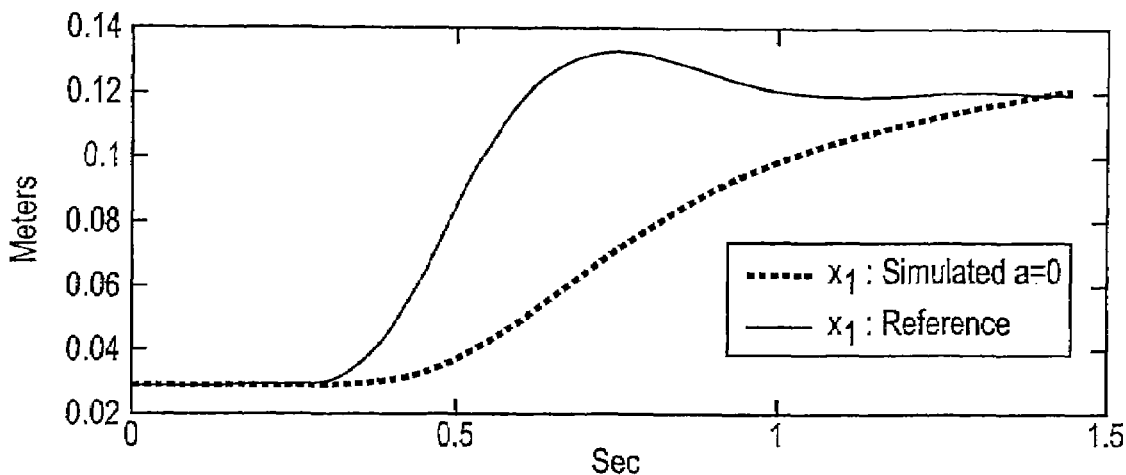
FIGS. 8A-8C are graphs illustrating tracking accuracy for the displacement of the ankle joint of FIG. 7 using small feedback gains and ignoring accelerations.
Figure 8B:
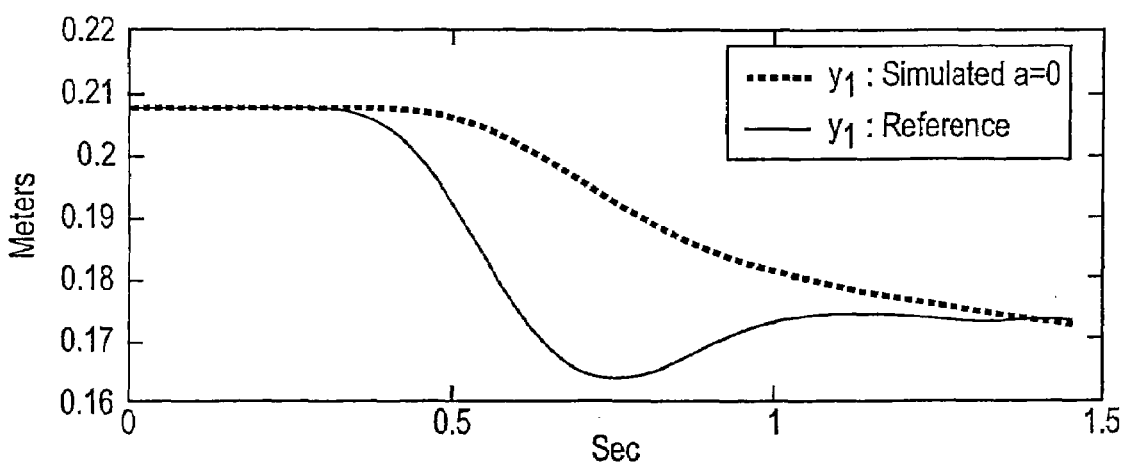
Figure 8C:
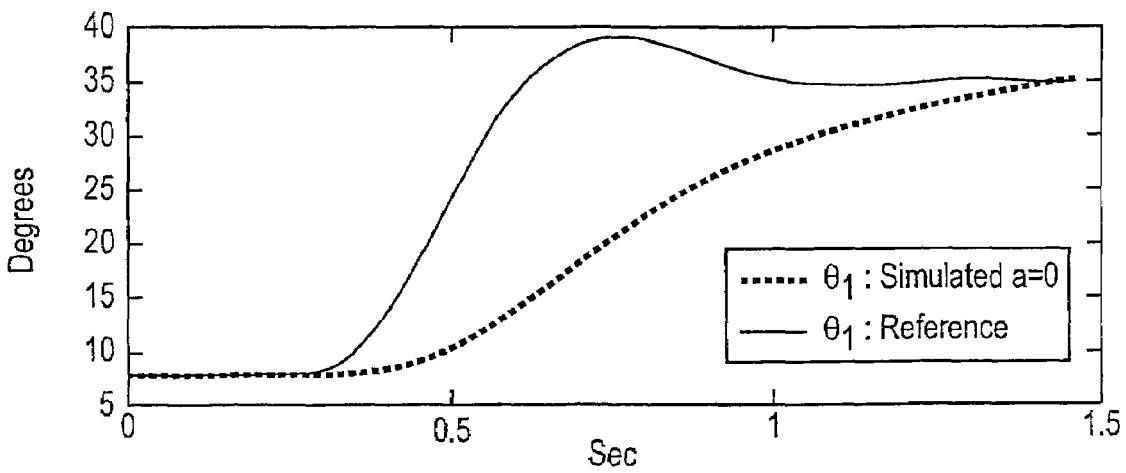
Figure 9A:
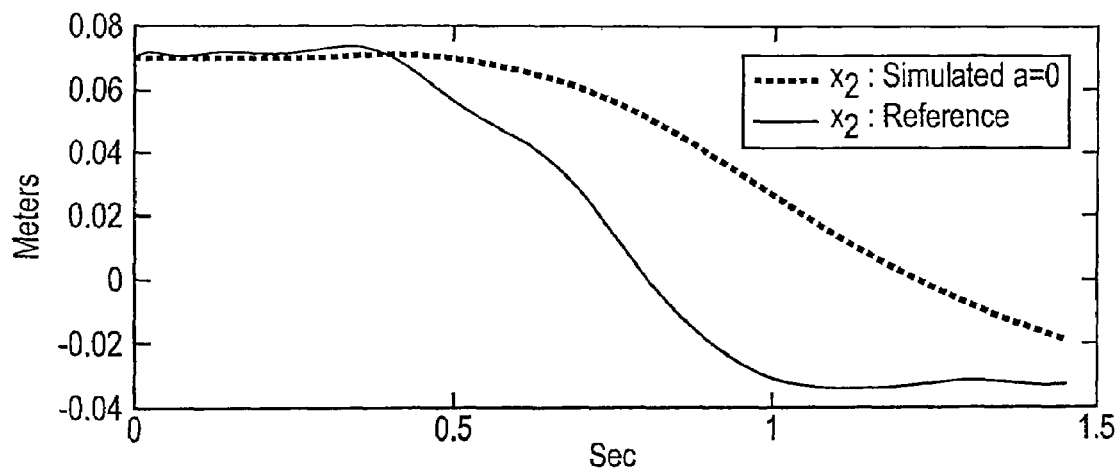
FIGS. 9A-9C are graphs illustrating tracking accuracy for the displacement of the knee joint of FIG. 7 using small feedback gains and ignoring accelerations.
Figure 9B:
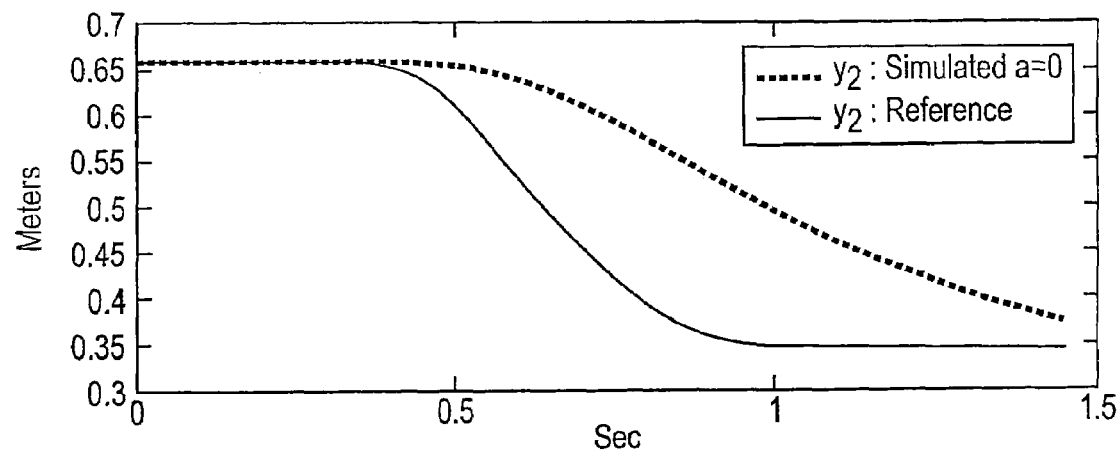
Figure 9C:
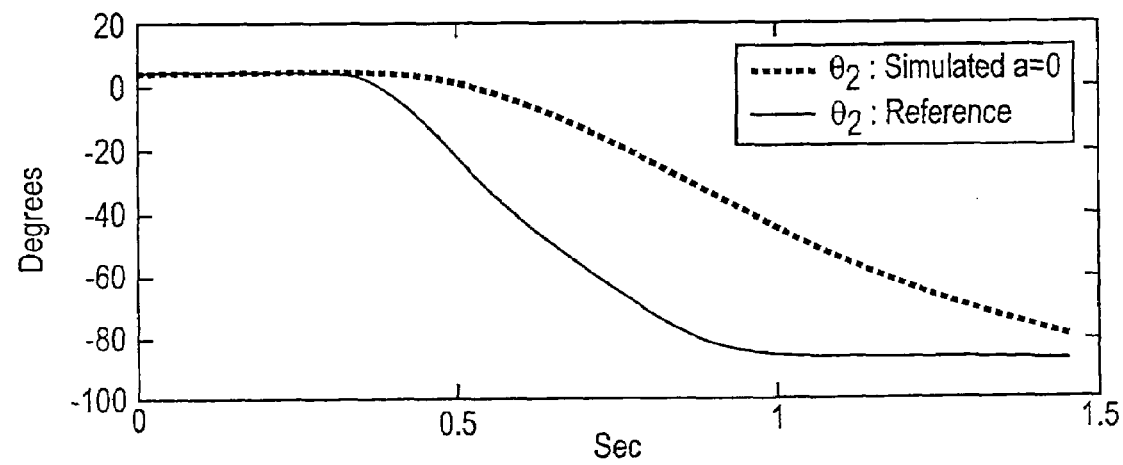
Figure 10A:
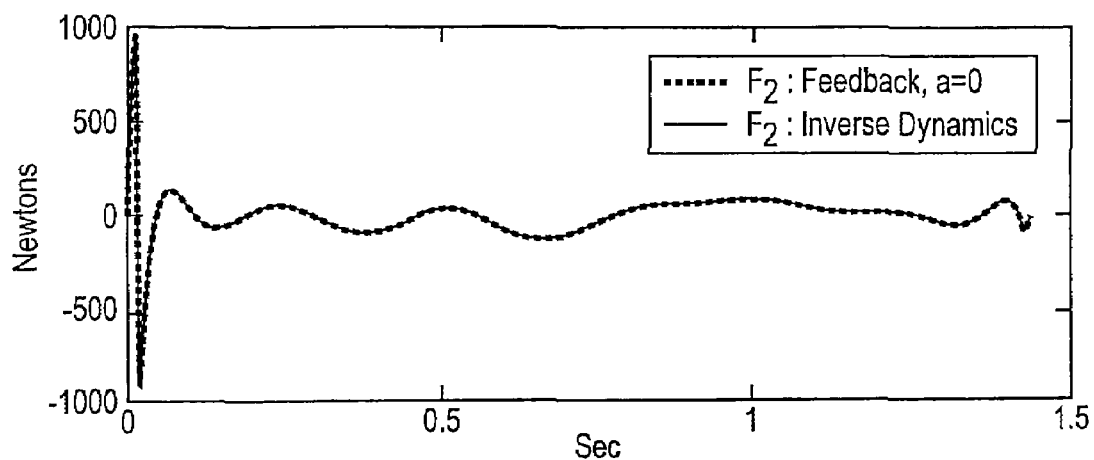
FIGS. 10A-10C are graphs illustrating tracking accuracy for the forces and moments of the knee joint of FIG. 7 using small feedback gains and ignoring accelerations.
Figure 10B:
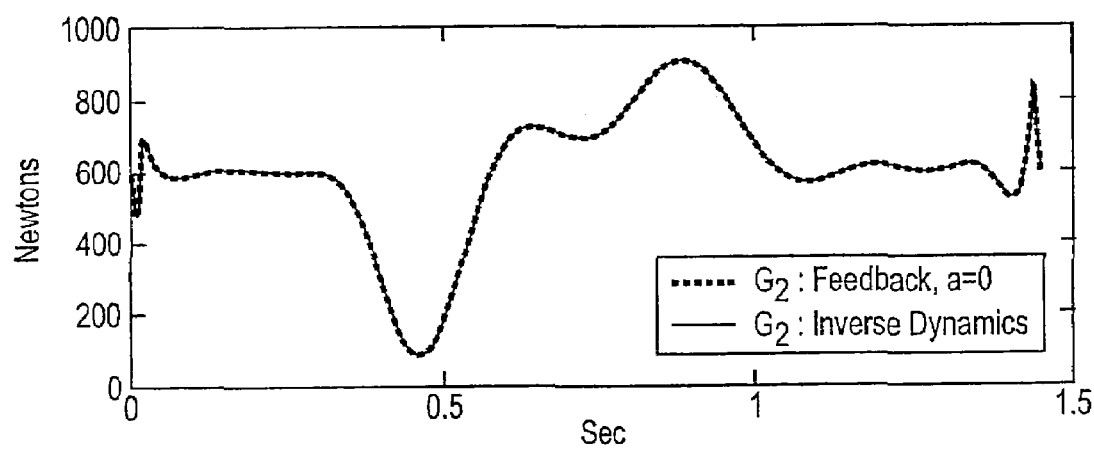
Figure 10C:
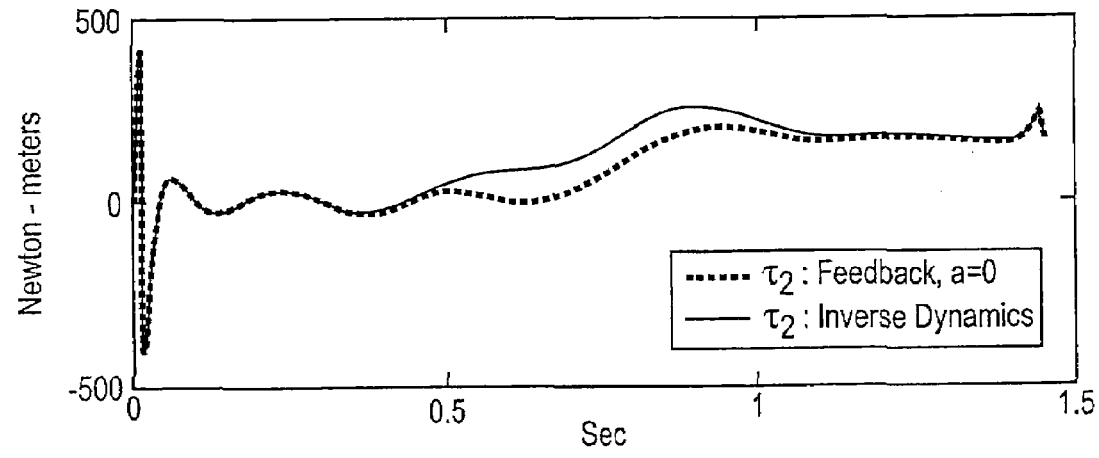
Figure 11A:
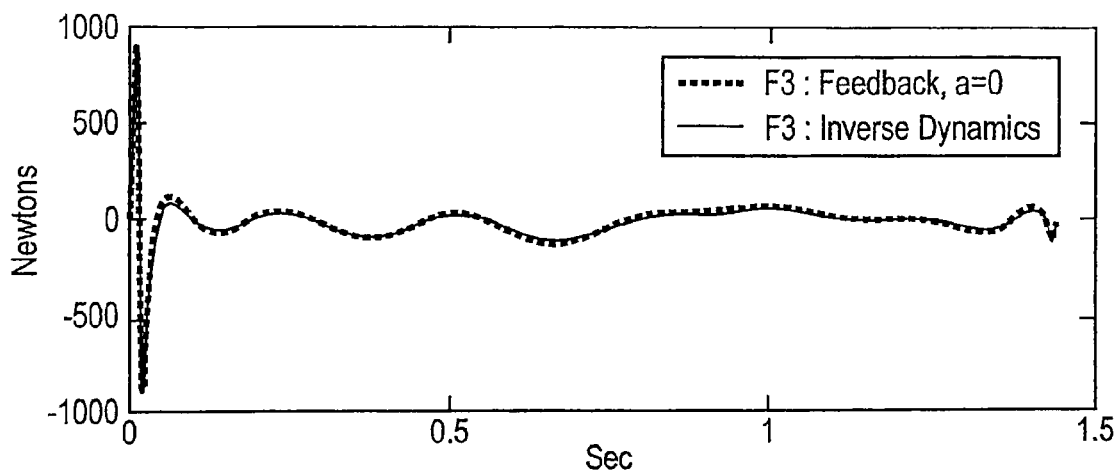
FIGS. 11A-11C are graphs illustrating tracking accuracy for the forces and moments of the hip joint of FIG. 7 using small feedback gains and ignoring accelerations.
Figure 11B:
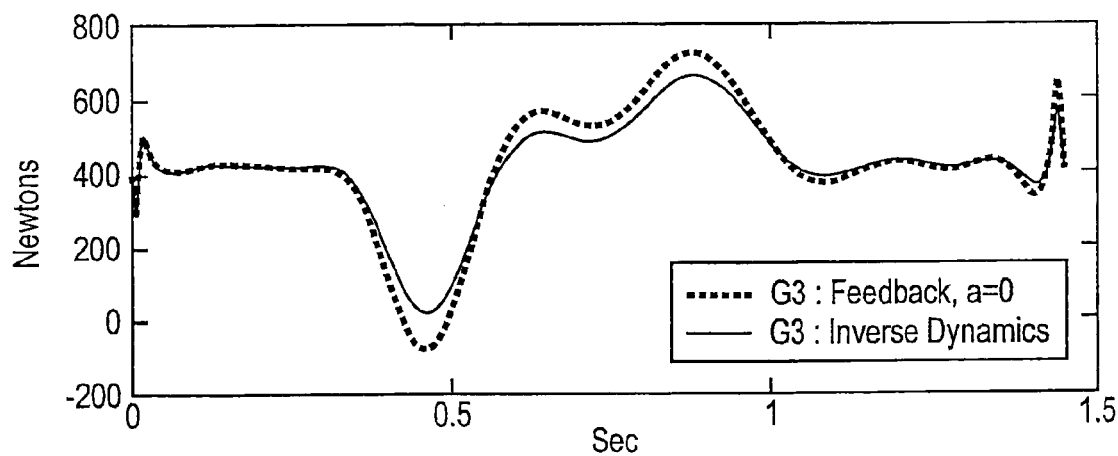
Figure 11C:
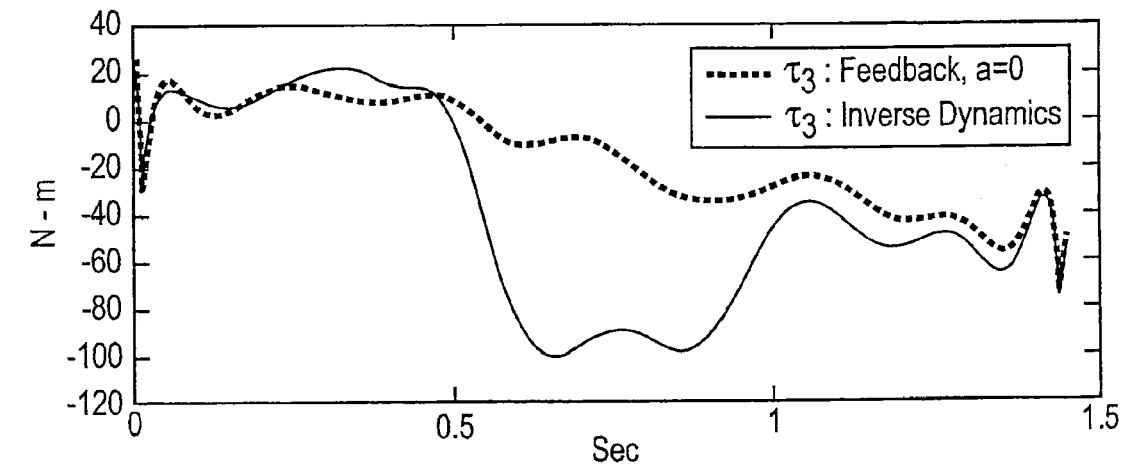
Figure 12A:
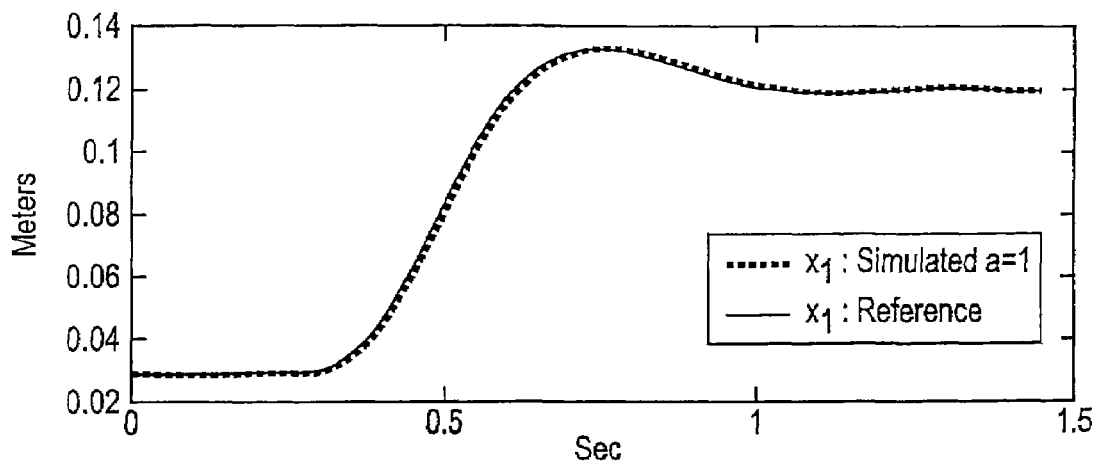
FIGS. 12A-12C are graphs illustrating tracking accuracy for the displacement of the ankle joint of FIG. 7 using small feedback gains and including accelerations.
Figure 12B:
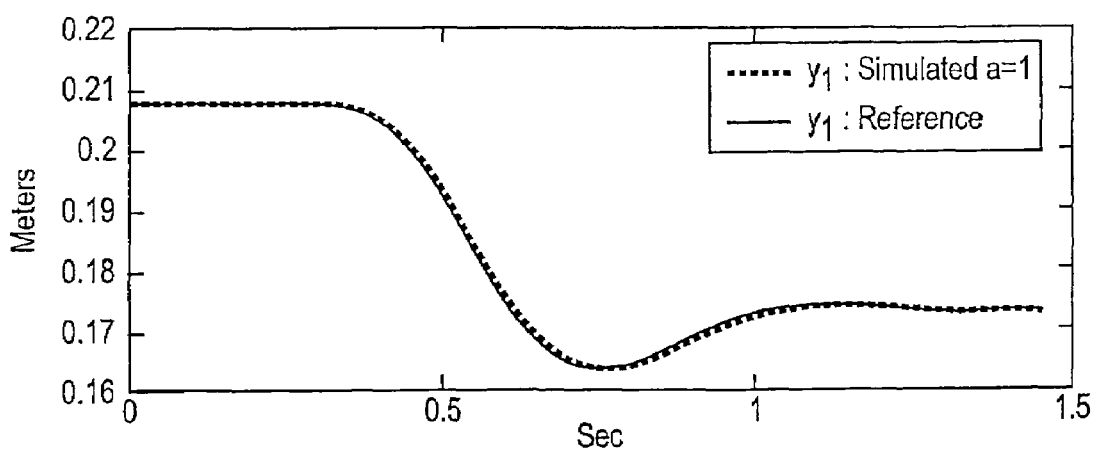
Figure 12C:
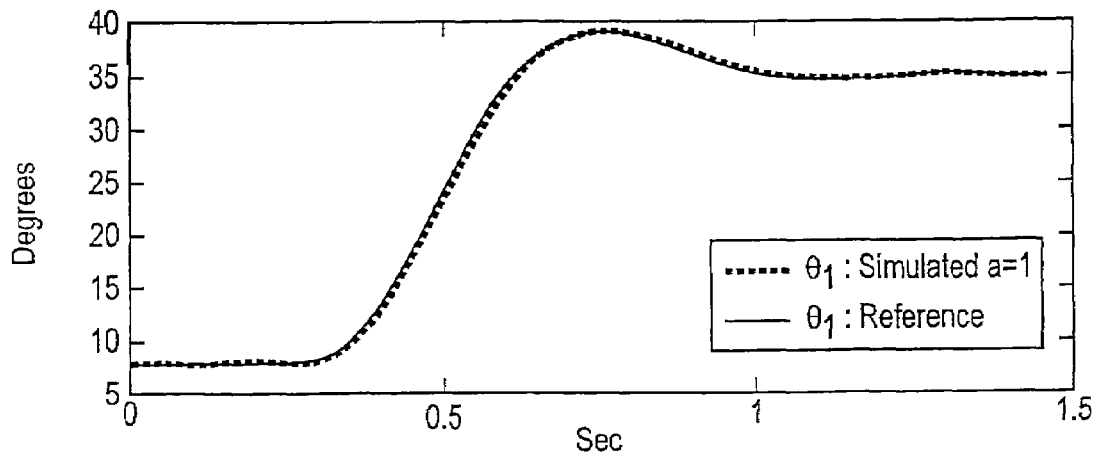
Figure 13A:
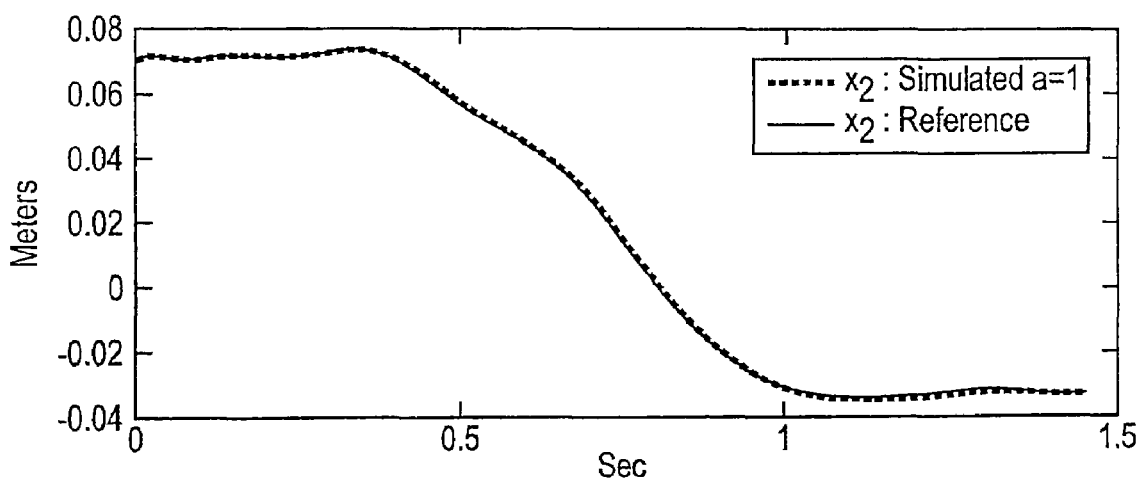
FIGS. 13A-13C are graphs illustrating tracking accuracy for the displacement of the knee joint of FIG. 7 using small feedback gains and including accelerations.
Figure 13B:
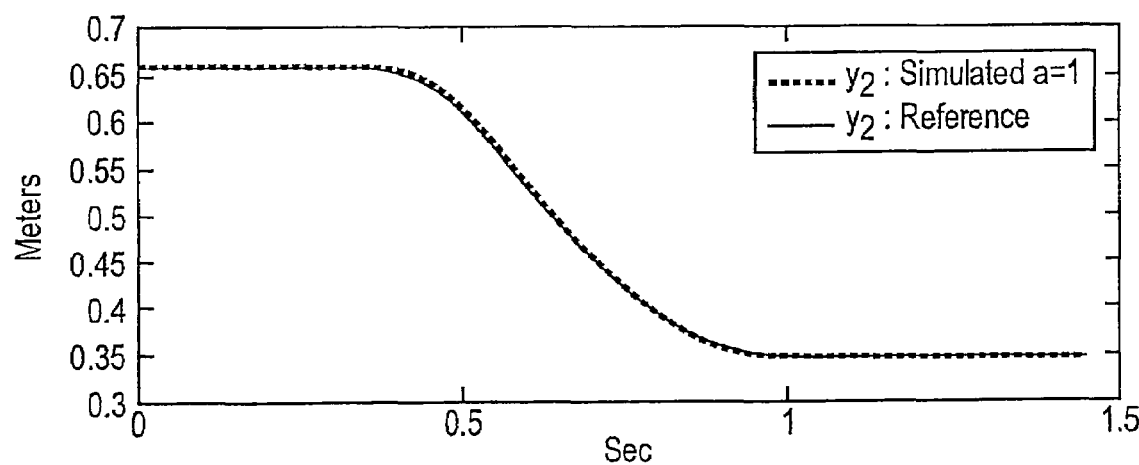
Figure 13C:
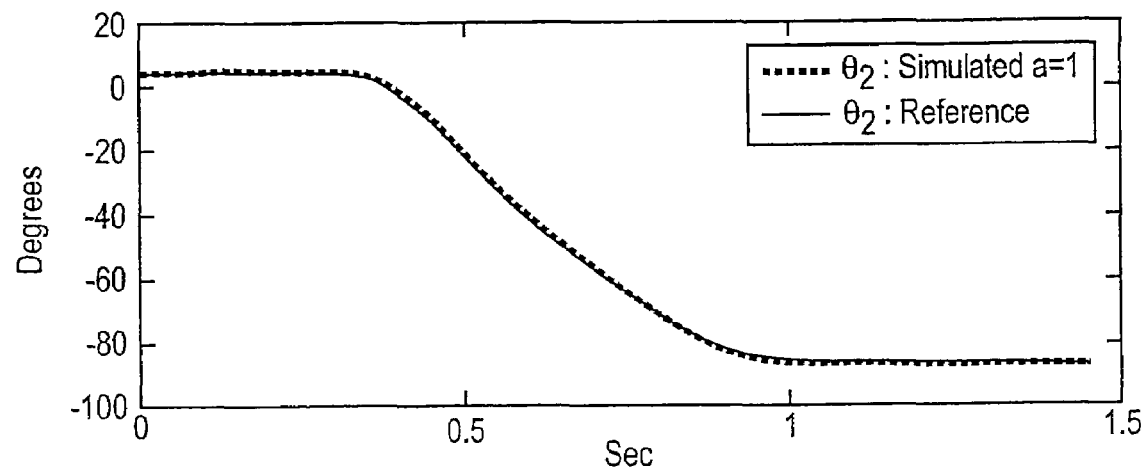
Figure 14A:
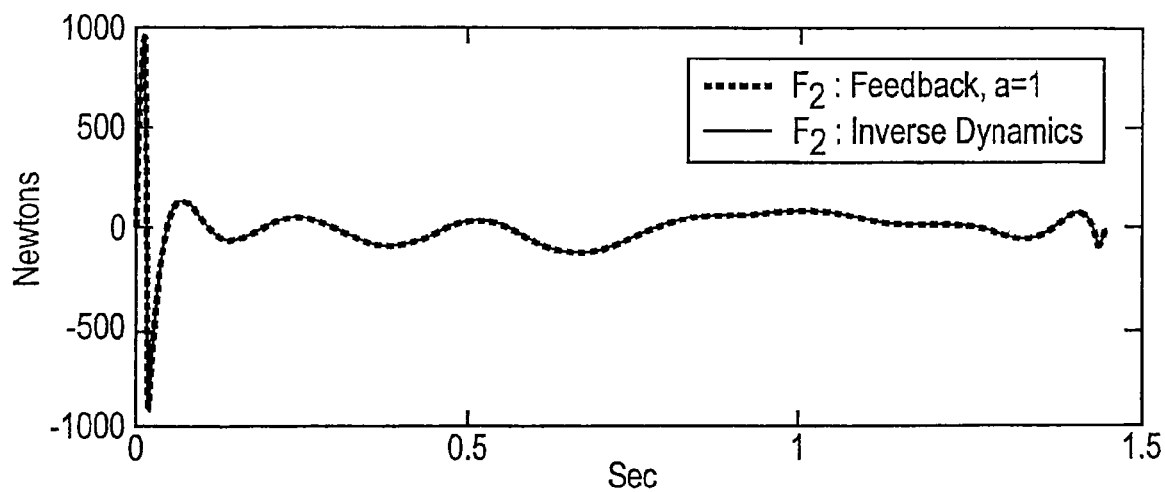
FIGS. 14A-14C are graphs illustrating tracking accuracy for the forces and moments of the knee joint of FIG. 7 using small feedback gains and including accelerations.
Figure 14B:
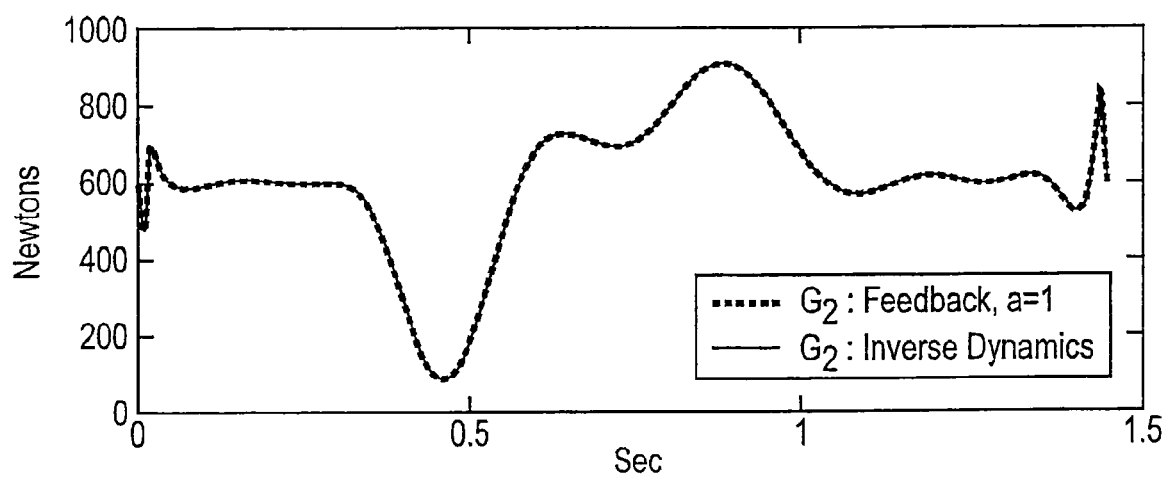
Figure 14C:
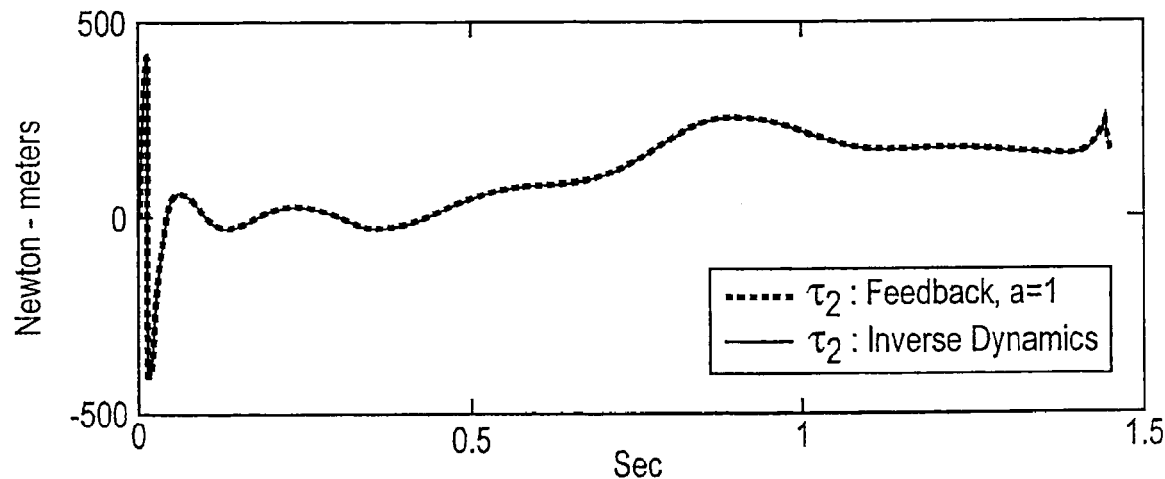
Figure 15A:
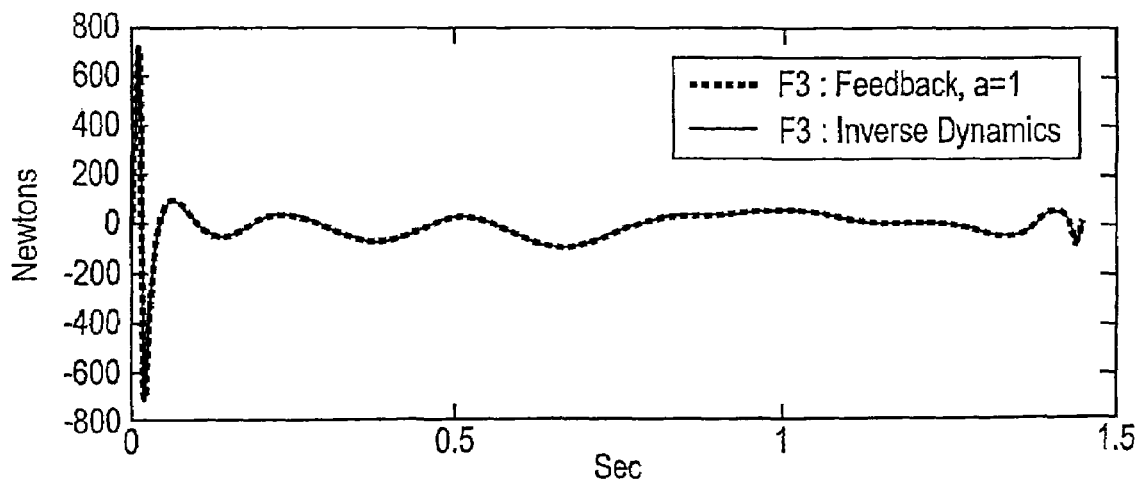
FIGS. 15A-15C are graphs illustrating tracking accuracy for the forces and moments of the hip joint of FIG. 7 using small feedback gains and including accelerations.
Figure 15B:
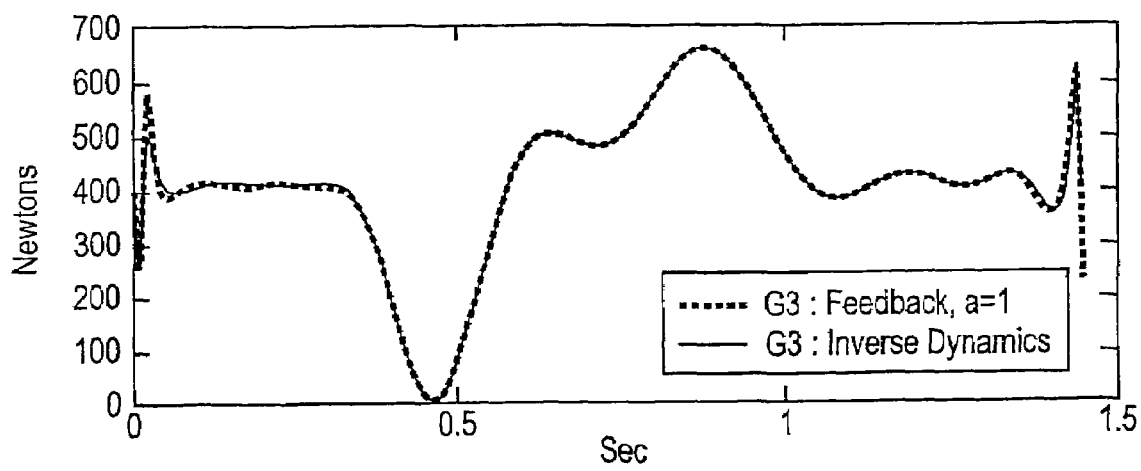
Figure 15C:
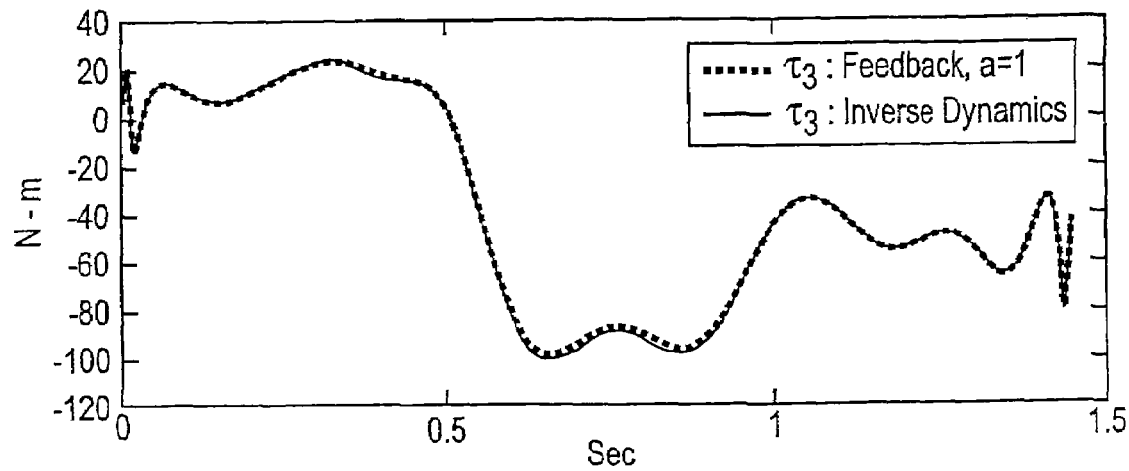
Figure 16A:
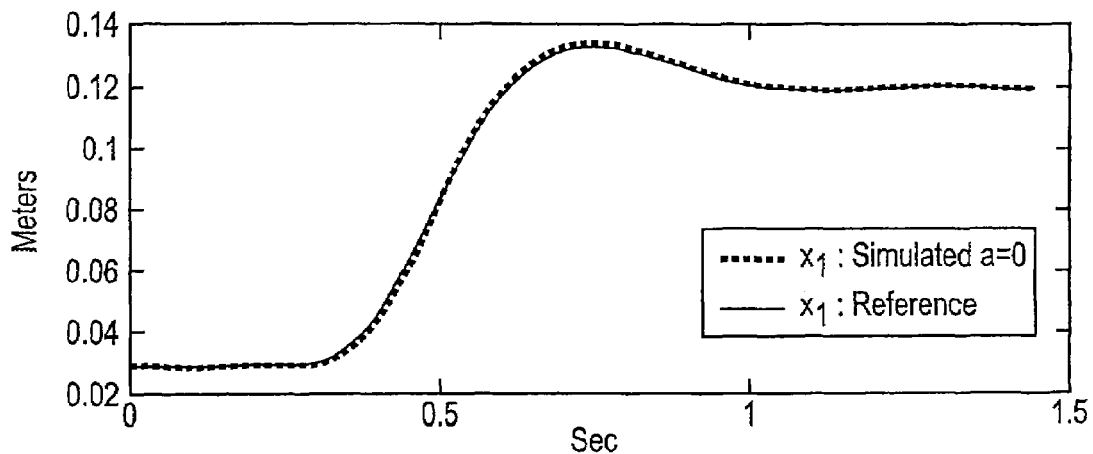
FIGS. 16A-16C are graphs illustrating tracking accuracy for the displacement of the ankle joint of FIG. 7 using large feedback gains and ignoring accelerations.
Figure 16B:
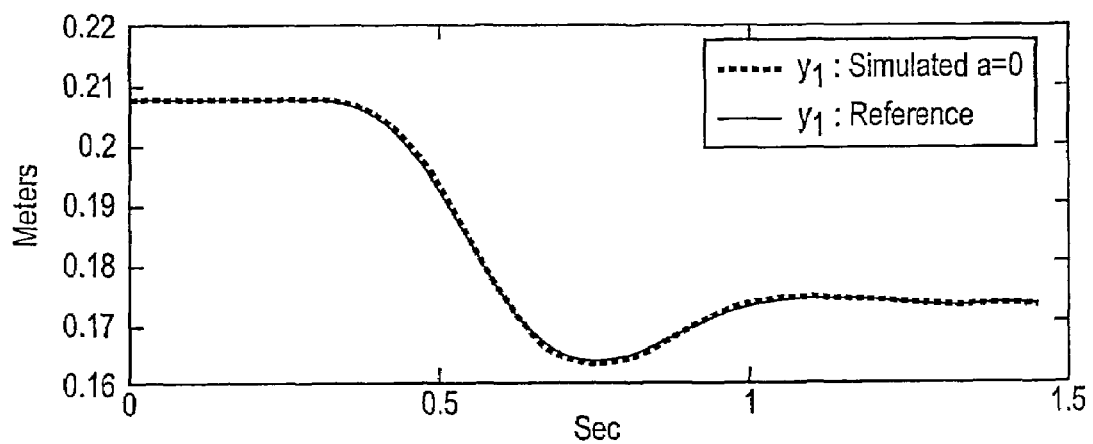
Figure 16C:
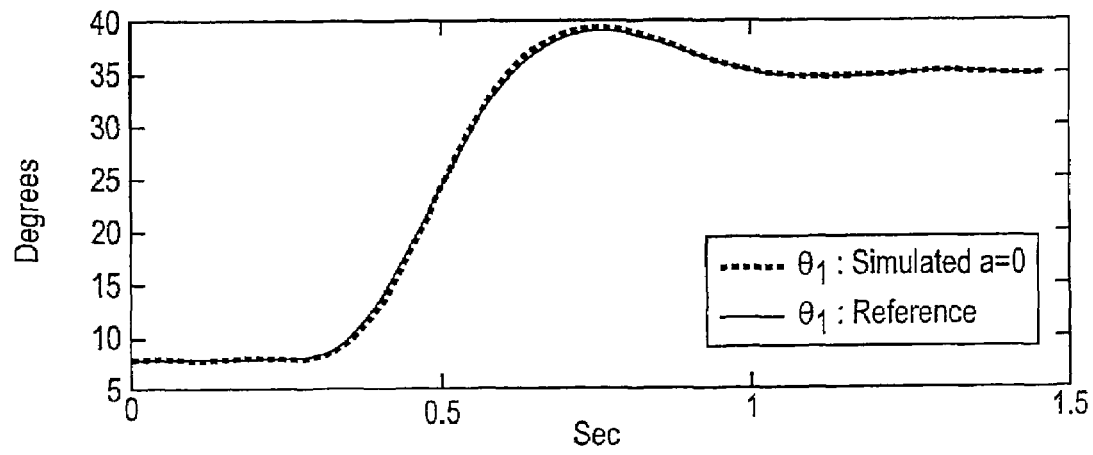
Figure 17A:
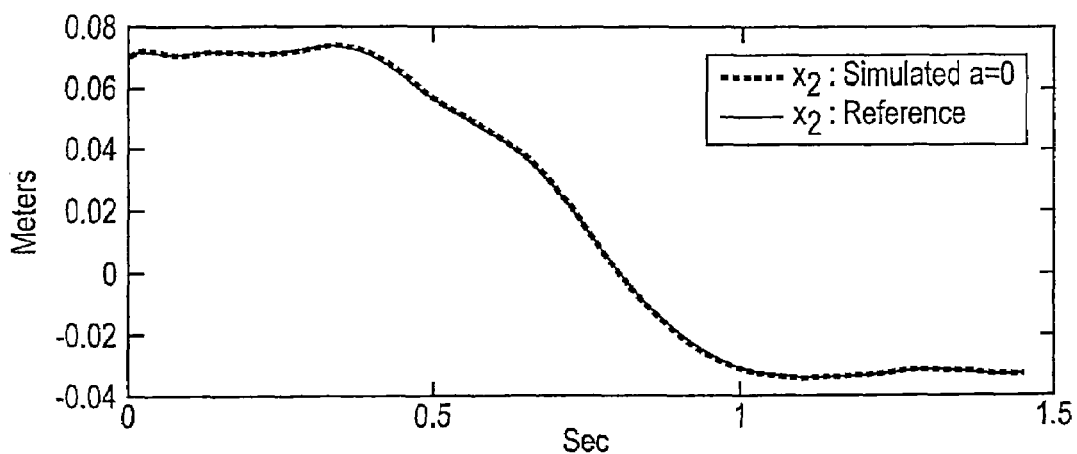
FIGS. 17A-17C are graphs illustrating tracking accuracy for the displacement of the knee joint of FIG. 7 using large feedback gains and ignoring accelerations.
Figure 17B:
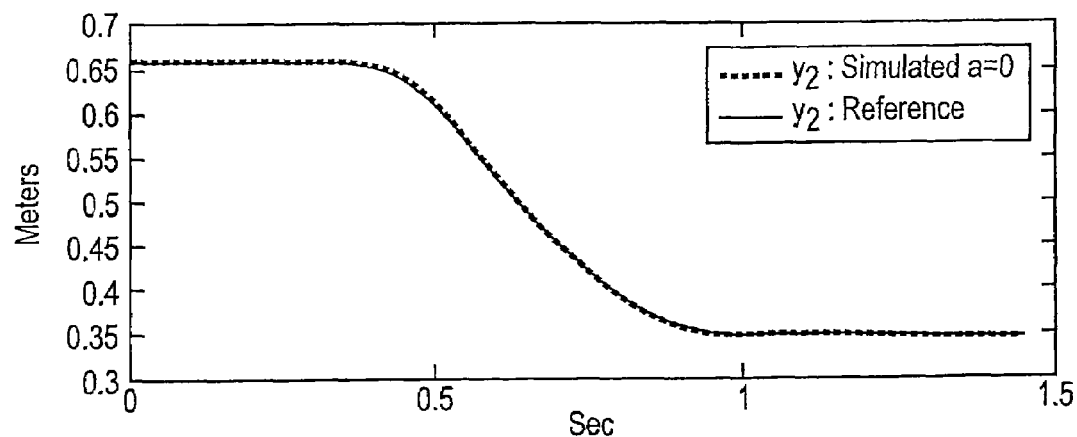
Figure 17C:
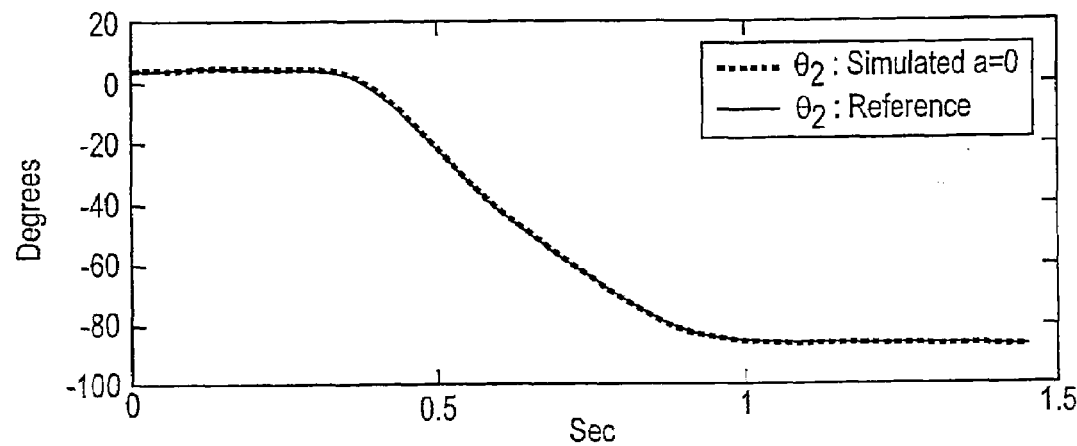
Figure 18A:
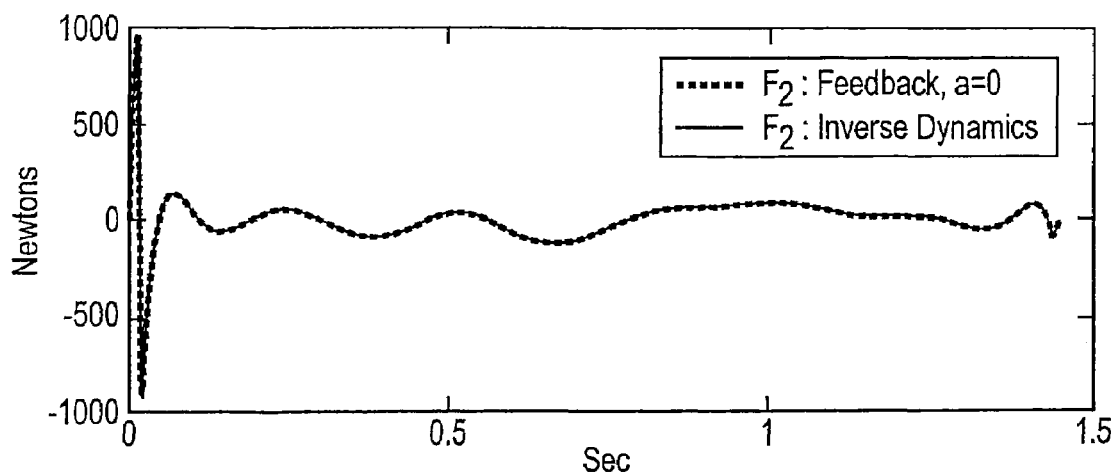
FIGS. 18A-18C are graphs illustrating tracking accuracy for the forces and moments of the knee joint of FIG. 7 using large feedback gains and ignoring accelerations.
Figure 18B:
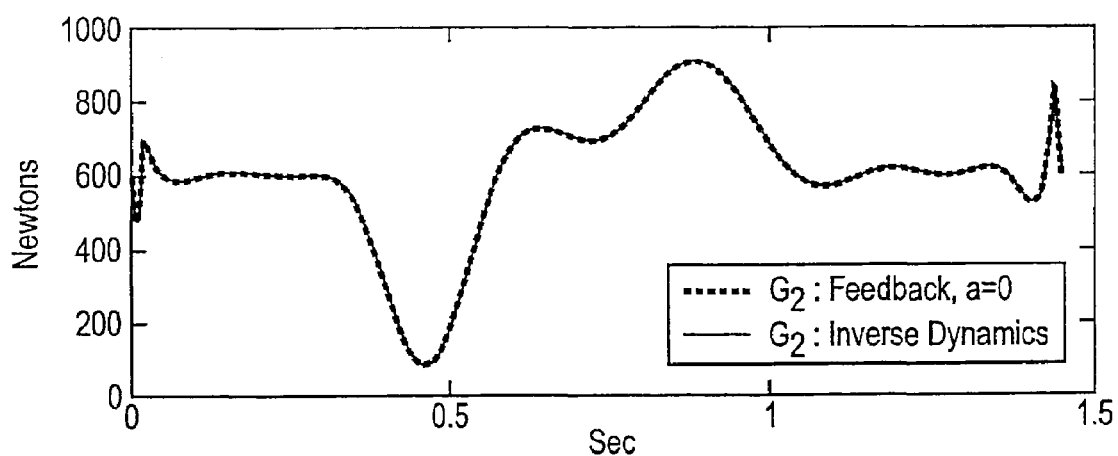
Figure 18C:
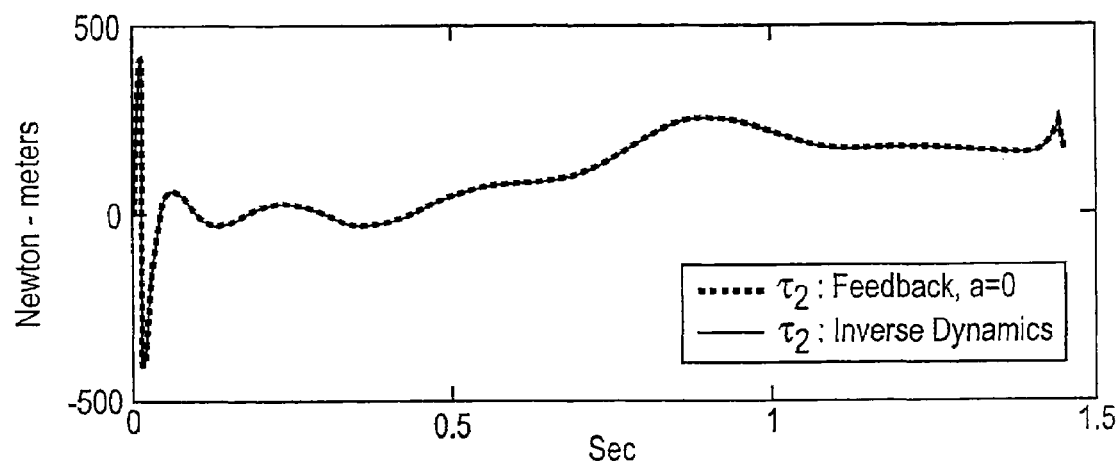
Figure 19A:
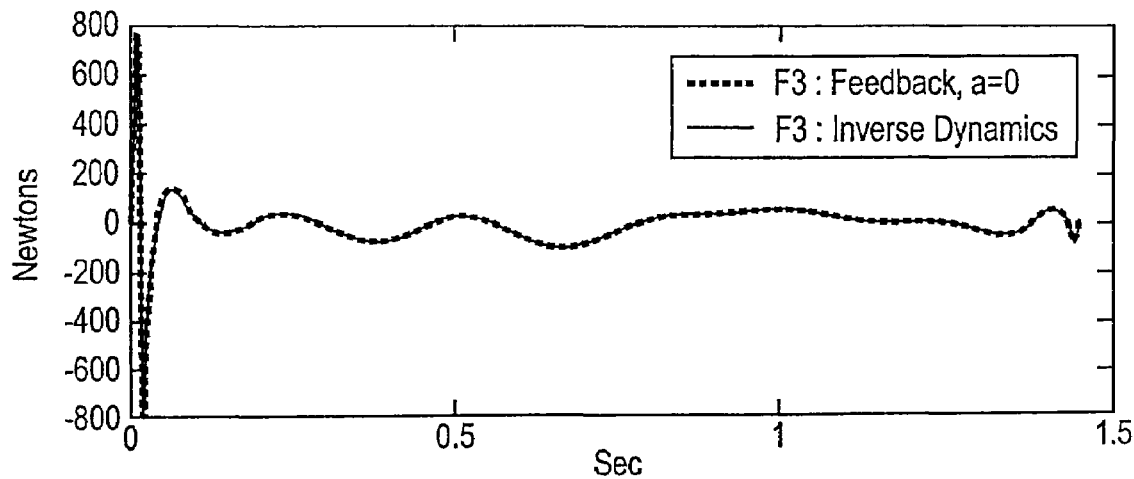
FIGS. 19A-19C are graphs illustrating tracking accuracy for the forces and moments of the hip joint of FIG. 7 using large feedback gains and ignoring accelerations.
Figure 19B:
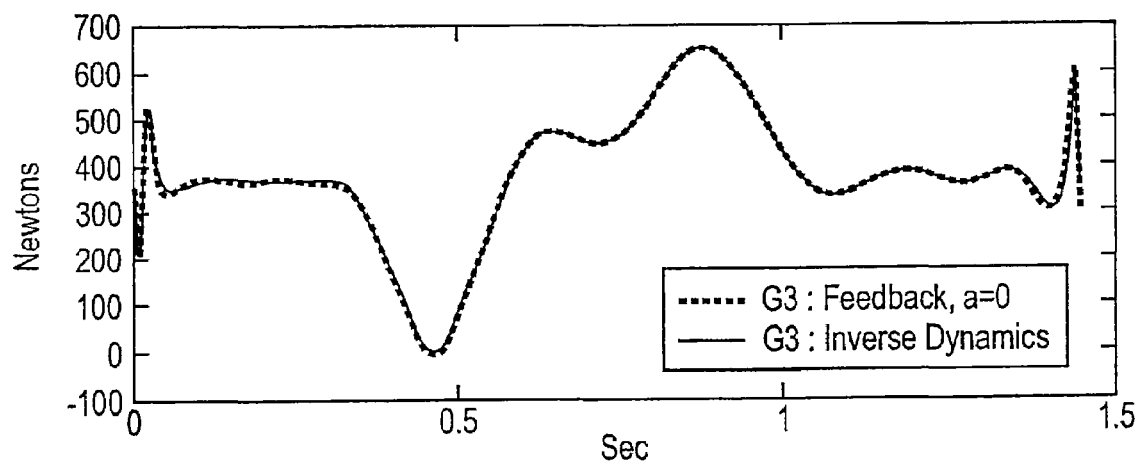
Figure 19C:
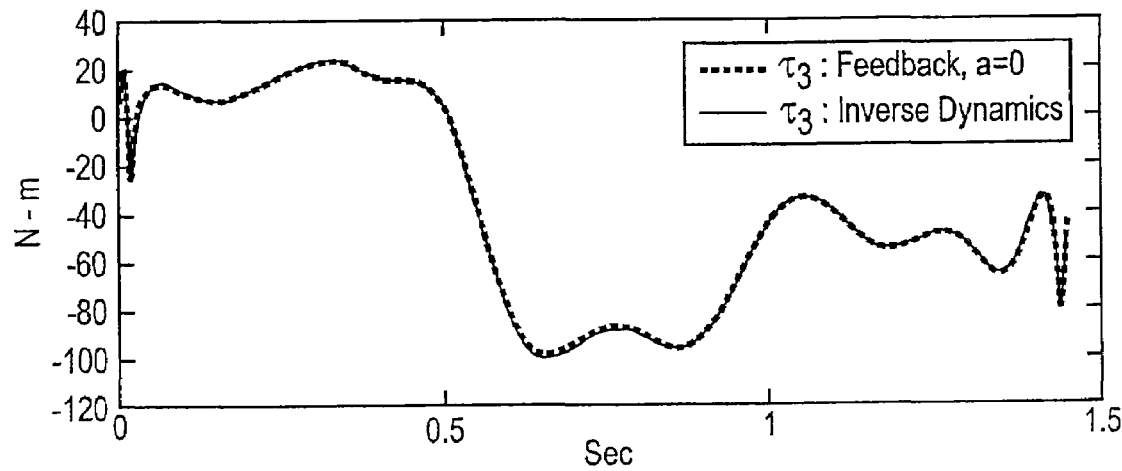
Figure 20A:
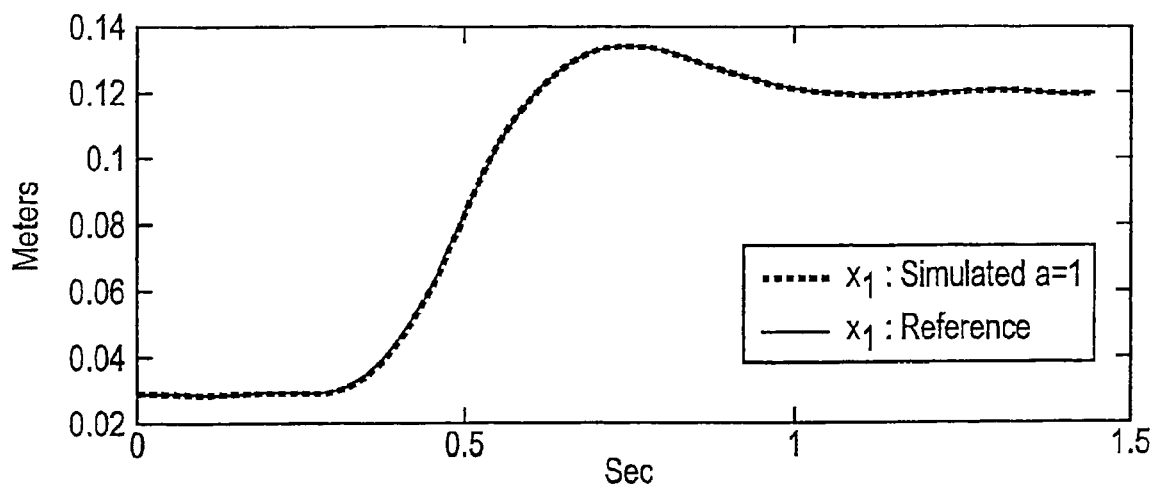
FIGS. 20A-20C are graphs illustrating tracking accuracy for the displacement of the ankle joint of FIG. 7 using large feedback gains and including accelerations.
Figure 20B:
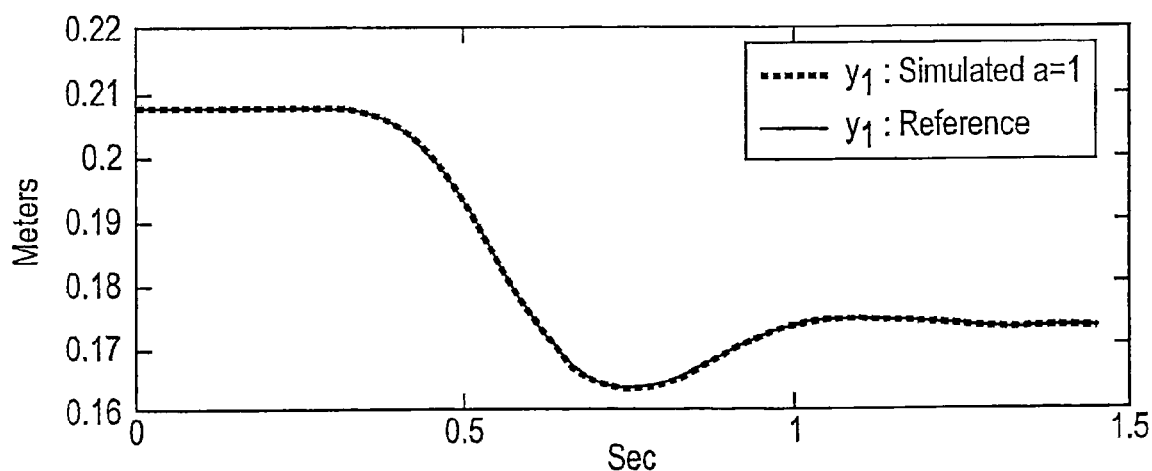
Figure 20C:
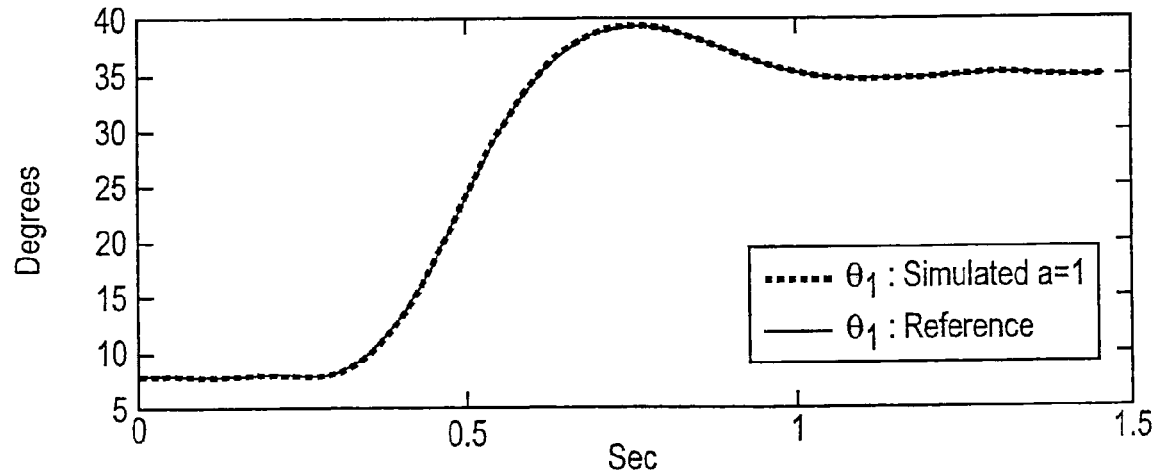
Figure 21A:
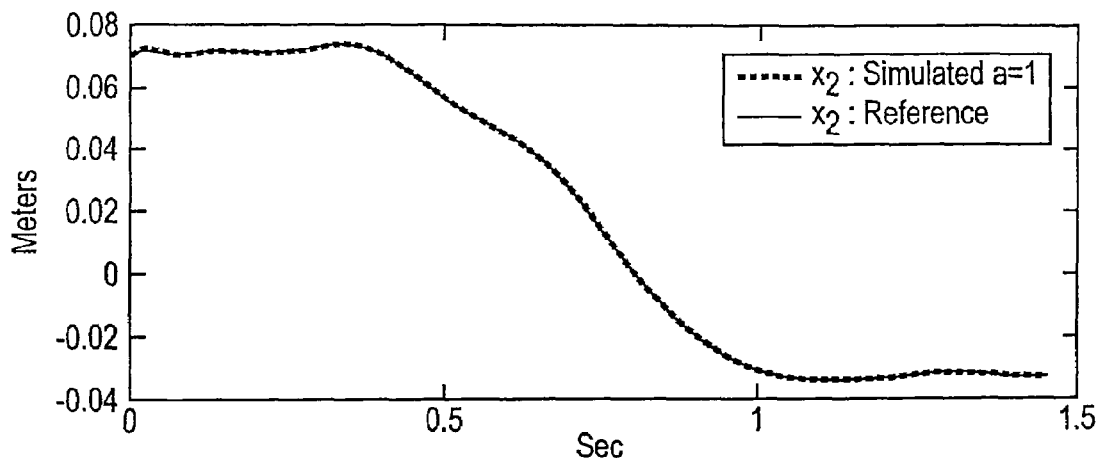
FIGS. 21A-21C are graphs illustrating tracking accuracy for the displacement of the knee joint of FIG. 7 using large feedback gains and including accelerations.
Figure 21B:
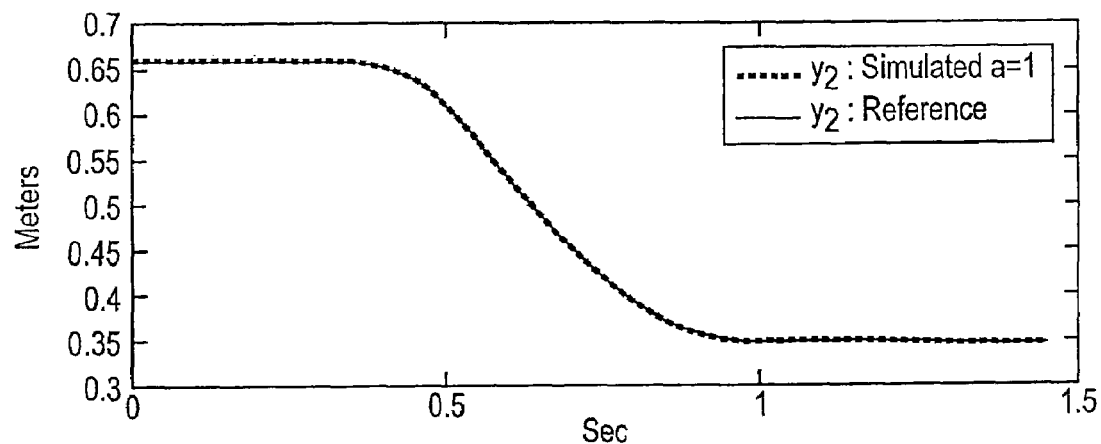
Figure 21C:
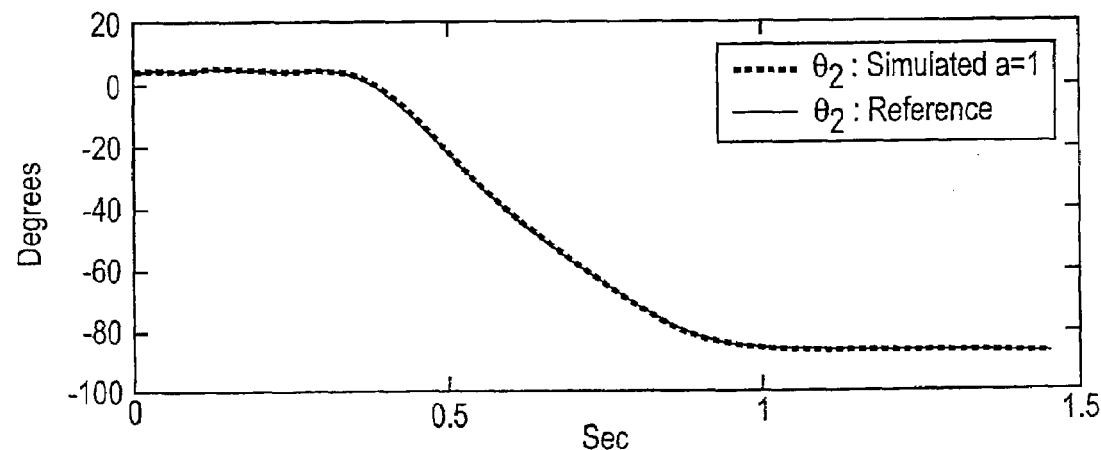
Figure 22A:
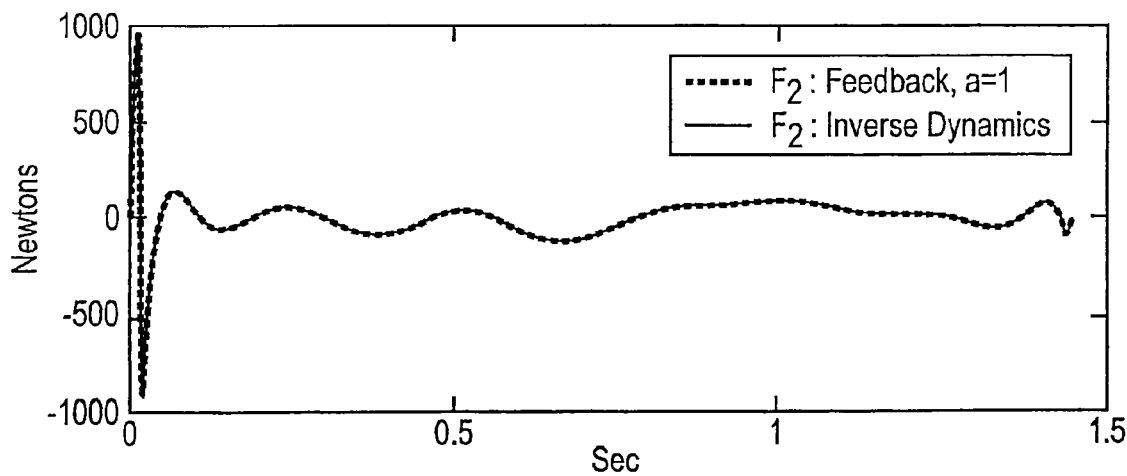
FIGS. 22A-22C are graphs illustrating tracking accuracy for the forces and moments of the knee joint of FIG. 7 using large feedback gains and including accelerations.
Figure 22B:
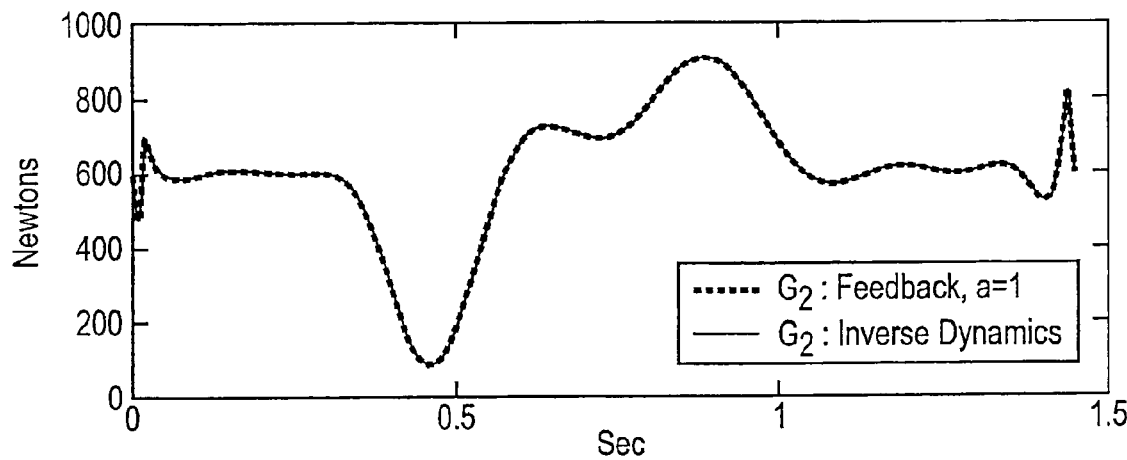
Figure 22C:
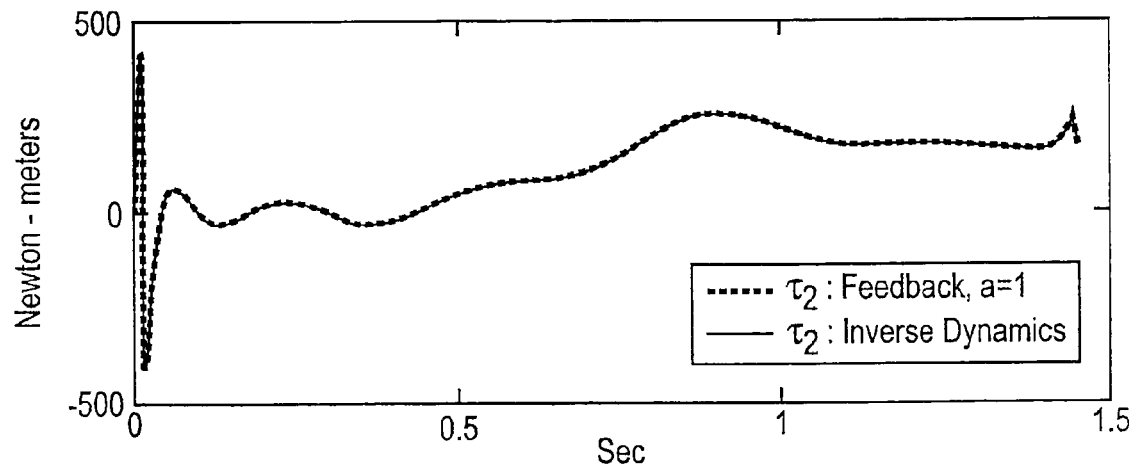
Figure 23A:
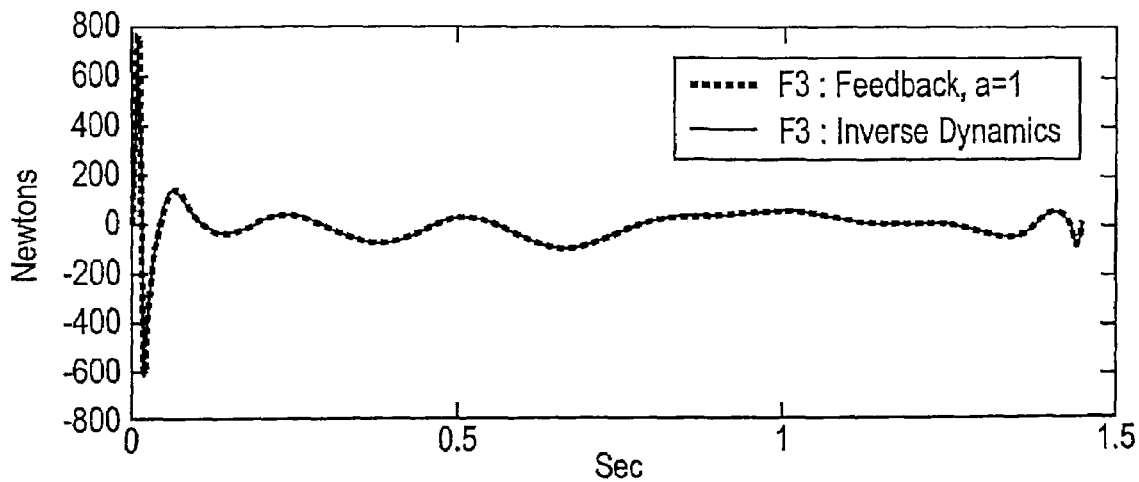
FIGS. 23A-23C are graphs illustrating tracking accuracy for the forces and moments of the hip joint of FIG. 7 using large feedback gains and including accelerations.
Figure 23B:
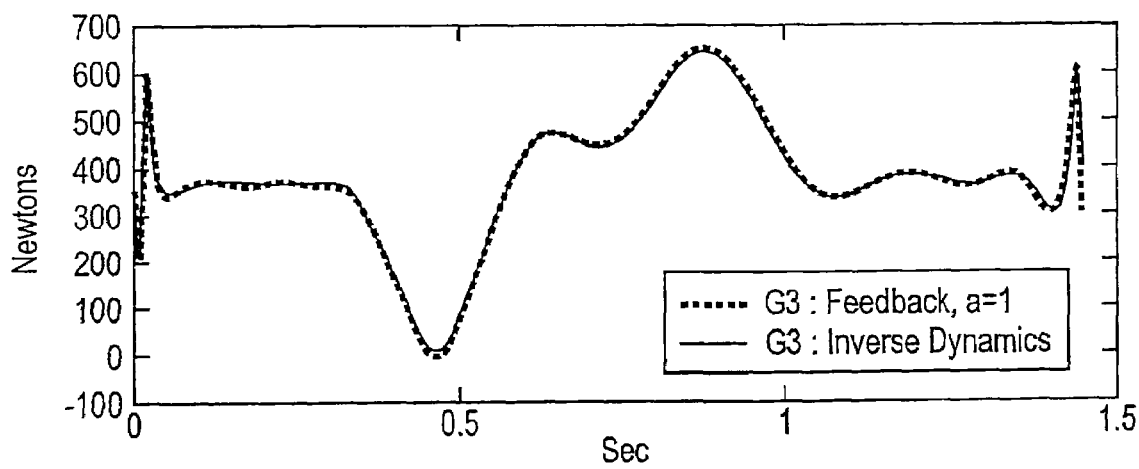
Figure 23C:
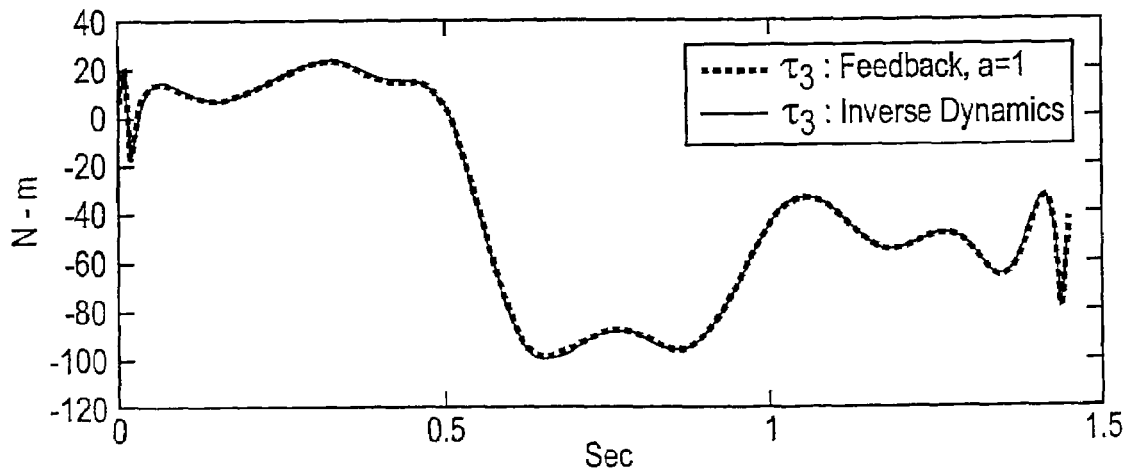

FIG. 7 is a free body diagram illustrating a three segment, two-dimensional open chain system. The three segments include human shank 705, thigh 710, and trunk 715 segments. Ankle joint 720 is assumed to be hinged to the ground. Knee joint 725 connects shank 705 and thigh 710. Hip joint 730 connects thigh 710 and trunk 715. A simulation is described to demonstrate the performance of an embodiment of the tracking system for estimating joint forces and moments. The selected system parameters are typical for those of an average male with a height of 1.7 m and a body weight of 74 kg. The simulated motion considered here is a squatting motion about the ankle, knee, and hip joints, 720, 725, and 730. The objective is to use $U_1$ as a constraint to initiate the recursion, and to compute iteratively $U_2 = [F_2 \ G_2 \ \tau_2]^T$ and $U_3 = [F_3 \ G_3 \ \tau_3]^T$. The required vector of joint moments and forces is denoted by $U = [u_1 \ u_2 \ u_3]^T$. To generate the reference trajectories, the recorded motion of an average male performing the squatting motion is used. One skilled in the art will appreciate how to capture and to record a squatting motion using conventional techniques. The Newton-Euler equations of motion for each isolated body segment are described as follows in Equations 25-33:

Segment 1: Shank 705

$$m_1\ddot{x}_1 = F_1 - F_2 \tag{25}$$

$$m_1\ddot{y}_1 = G_1 - G_2 - m_1 g \tag{26}$$

$$I_1\ddot{\theta}_1 = -F_1 k_1 \cos(\theta_1) + G_1 k_1 \sin(\theta_1) - F_2(l_1-k_1)\cos(\theta_1) + G_2(l_1-k_1)\sin(\theta_1) + u_1 - u_2 \tag{27}$$

Segment 2: Thigh 710

$$m_2\ddot{x}_2 = F_2 - F_3 \tag{28}$$

$$m_2\ddot{y}_2 = G_2 - G_3 - m_2 g \tag{29}$$

$$I_2\ddot{\theta}_2 = -F_2 k_2 \cos(\theta_2) + G_2 k_2 \sin(\theta_2) - F_3(l_2-k_2)\cos(\theta_2) + G_3(l_2-k_2)\sin(\theta_2) + u_2 - u_3 \tag{30}$$

Segment 3: Trunk 715

$$m_3\ddot{x}_3 = F_3 \tag{31}$$

$$m_3\ddot{y}_3 = G_3 - m_3 g \tag{32}$$

$$I_3\ddot{\theta}_3 = -F_3 k_3 \cos(\theta_3) + G_3 k_3 \sin(\theta_3) + u_3 \tag{33}$$

The simulation is designed to compare tracking system performance with the traditional inverse dynamics approach.

The inputs include the kinematic data for the squatting motion as well as ground reaction forces. In the described simulation, tracking system performance is examined for two cases: when the acceleration estimates are included (a=1 in FIG. 5), and when the acceleration estimated are ignored (a=0 in FIG. 5). To maintain consistency, it is assumed that the ground reaction measurements are ideal and are obtained analytically. The analytically computed ground reaction vector $U_1=[F_1\ G_1\ \tau_1]^T$ is obtained using the recursion equations starting from trunk 715 and working toward the ground as described above. Using $U_1$ as a constraint, $U_2$ and $U_3$ are recursively estimated. The simulation is performed for two different sets of feedback gains matrices, which produce a critically damped response. Simulation results are illustrated in FIGS. 8-23.

In the simulations illustrated by FIGS. 8-15, the small feedback gain values of Equation 34 are used. The reference joint displacement data has been smoothed for convenience of illustration. As described above, including the acceleration estimates is often undesirable because inverse dynamics analysis requires calculation of higher order derivatives that cause erroneous results. Each of the dotted curves of FIGS. 8-11 correspond to simulated tracking accuracy where desired accelerations are ignored (a=0). In both the displacement graphs of FIGS. 8 and 9 and the force and moment graphs of FIGS. 10 and 11, when accelerations are ignored, the simulated result using small feedback gains exhibits poor tracking performance. As illustrated in FIGS. 12-15, the tracking performance and the estimated joint moments are exceptionally good when the desired accelerations are included (a=1).

$$K_p = K_v = \begin{bmatrix} 1 & 0 & 0 \\ 0 & 1 & 0 \\ 0 & 0 & 1 \end{bmatrix} \quad (34)$$

In contrast to FIGS. 8-11, the simulations illustrated by FIGS. 16-19 achieve excellent tracking performance. In these simulations, the feedback gains are increased to achieve improved results for the case when desired accelerations are ignored (a=0). Equations 35 and 36 set forth the feedback gain parameters. In both the displacement graphs of FIGS. 16 and 17 and the force and moment graphs of FIGS. 18 and 19, each of the dotted curves representing simulated tracking accuracy where acceleration estimates are excluded (a=0) is substantially indistinguishable from the reference data. Embodiments of nonlinear feedback estimation of joint forces and moments are illustrated to be effective without requiring, for example, higher order derivatives of noisy measurement data.

$$K_p = \begin{bmatrix} 1600 & 0 & 0 \\ 0 & 1600 & 0 \\ 0 & 0 & 1600 \end{bmatrix} \quad (35)$$

$$K_v = \begin{bmatrix} 80 & 0 & 0 \\ 0 & 80 & 0 \\ 0 & 0 & 80 \end{bmatrix} \quad (36)$$

Figure 24:
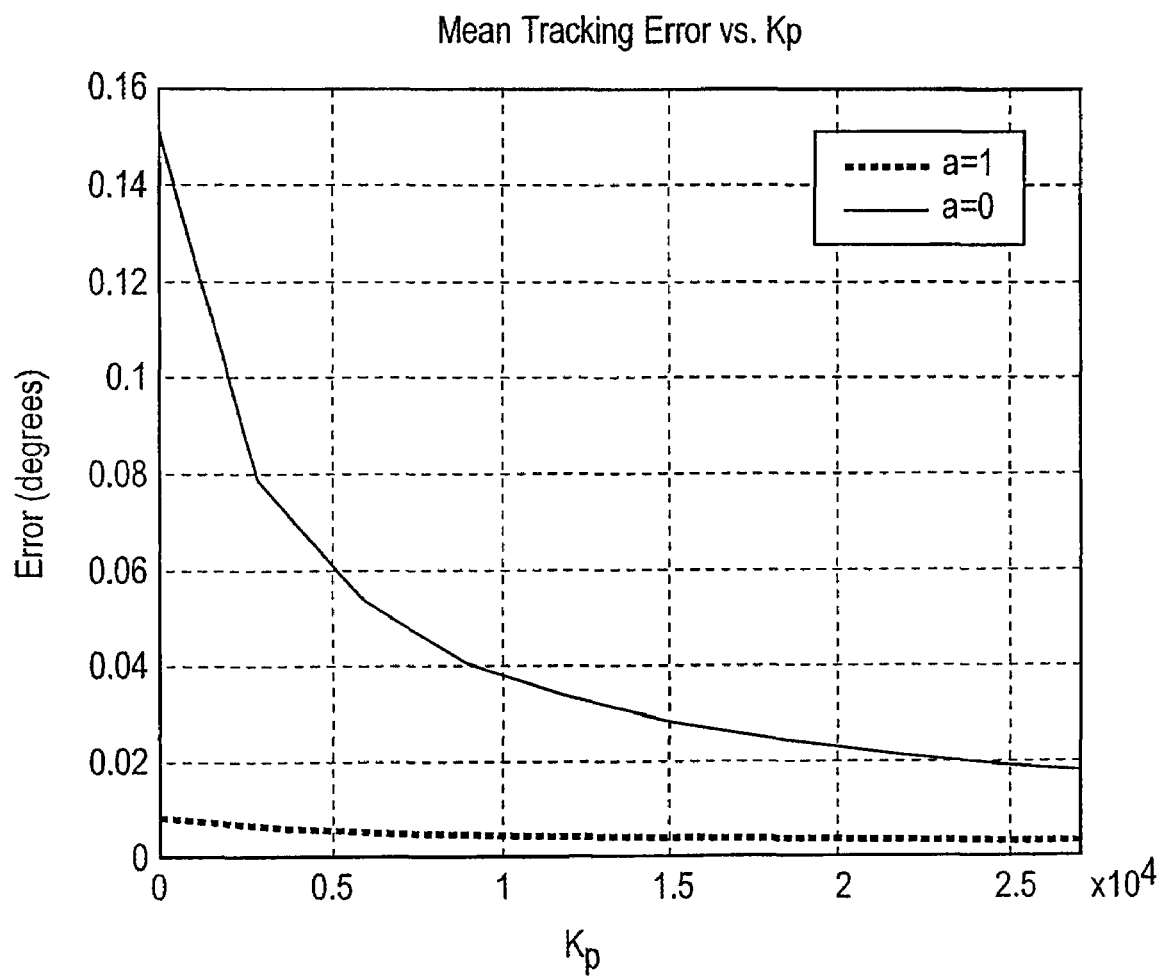
FIG. 24 is a graph illustrating tracking error for the displacement of the ankle joint of FIG. 7.

FIG. 24 is a graph illustrating tracking error for the displacement of the ankle joint of FIG. 7. In the illustration, the dotted curve corresponds to the absolute value of the mean tracking error when the desired accelerations are included (a=1). The solid curve corresponds to the absolute value of the mean tracking error when acceleration estimates are excluded (a=0). For each of several values of $K_p$, the mean tracking error (over the duration of the simulation) between the desired and simulated angle was computed. For each of the data points, the absolute value of the mean error was calculated to generate the graph. In the illustrated case where acceleration estimates are excluded (a=0), the mean tracking error for the displacement of ankle joint 720 converges to zero with increasing values of $K_p$. Mean tracking error for other angles and states are not specifically illustrated because one skilled in the art will recognize that similar results are produced.

The present invention may be embodied in many different forms and should not be construed as limited to the embodiments set forth herein. Rather these embodiments are provided so that this disclosure will be thorough and complete and will fully convey the invention to those skilled in the art. For example, one skilled in the art will appreciate that the tracking systems and methods described can be extended to three-dimensional systems. Further, conventional muscle force distribution methods can be embedded in, e.g., forward dynamics module 415 (FIG. 4). The output of a muscle force distribution module could then drive the forward simulation. Alternatively, a muscle force distribution module can tap the output of the inverse dynamics module 410 (FIG. 4) and not be used in the forward simulation.

Further, the apparatus and methods described are not limited to rigid bodies. One skilled in the art will recognize that the principles of the present invention can be applied to other systems that can be characterized by Equation 22. Embodiments of feedback estimation track data from systems governed by the second-order differential of a data set.

Having described preferred embodiments of Feedback Estimation of Joint Forces and Joint Movements (which are intended to be illustrative and not limiting), it is noted that modifications and variations can be made by persons skilled in the art in light of the above teachings. It is therefore to be understood that changes may be made in the particular embodiments of the invention disclosed that are within the scope and spirit of the invention as defined by the appended claims.

What is claimed is:

1. A method for determining an estimated joint load at a joint of interest in a system, the method comprising steps of:
   obtaining kinematic data for the system;
   obtaining an input force for the system;
   computing a modified acceleration using at least the kinematic data;
   performing an inverse dynamics analysis to determine the estimated joint load at the joint of interest by recursively estimating successive joint loads until the joint of interest is reached, the inverse dynamics analysis using at least the modified acceleration and the input force; and
   performing a forward dynamics analysis using the estimated joint load to determine simulated kinematic data for the system.

2. The method of claim 1 wherein the kinematic data comprises center of mass coordinates and a joint angle.

3. The method of claim 1 wherein the input force comprises a ground reaction force.

4. The method of claim 1 wherein the input force comprises force plate measurement.

5. The method of claim 1 wherein the input force is equal to zero.

6. The method of claim 1 wherein the input force acts at a point of contact on a segment of the system.

7. The method of claim 1 wherein the input force comprises at least one of an internal force and an internal moment.

8. The method of claim 1 wherein the input force comprises a joint torque.

9. The method of claim 1 wherein the step of computing the modified acceleration further comprises the steps of:
computing an error value representing a difference between the simulated kinematic data and the kinematic data; and
applying a feedback gain to the error value.

10. The method of claim 9 wherein the feedback gain comprises at least one of a positional feedback gain and a velocity feedback gain.

11. The method of claim 9, wherein applying the feedback gain to the error value comprises:
determining the feedback gain that achieves a critically damped response; and
applying the feedback gain to the error value.

12. The method of claim 1 wherein the step of performing a forward dynamics analysis further comprises performing an integration to determine the simulated kinematic data.

13. The method of claim 1, wherein the step of computing the modified acceleration further uses feedback of the simulated kinematic data.

14. The method of claim 1, wherein the step of performing the inverse dynamics analysis further uses feedback of the simulated kinematic data.

15. The method of claim 1, wherein the step of performing the forward dynamics analysis further uses feedback of the simulated kinematic data.

16. The method of claim 1 further comprising the steps of:
obtaining kinematic data for a second joint;
computing a second modified acceleration using at least the kinematic data for the second joint;
performing an inverse dynamics analysis to produce a second estimated joint load, the inverse dynamics analysis using at least the second modified acceleration and the estimated joint load; and
performing a forward dynamics analysis on the second estimated joint load to obtain simulated kinematic data for the second joint.

17. A computer readable medium including program instructions for determining an estimated joint load at a joint of interest in a system, comprising:
program instructions for obtaining kinematic data for the system;
program instructions for obtaining an input force for the system;
program instructions for computing a modified acceleration using at least the kinematic data;
program instructions for performing an inverse dynamics analysis to determine the estimated joint load at the joint of interest by recursively estimating successive joint loads until the joint of interest is reached, the inverse dynamics analysis using at least the modified acceleration and the input force; and
program instructions for performing a forward dynamics analysis using the estimated joint load to determine simulated kinematic data for the system.

18. The computer readable medium of claim 17 further comprising:
program instructions for computing an error value representing a difference between the simulated kinematic data and the kinematic data; and
program instructions for applying a feedback gain to the error value.

19. A method for determining an estimated joint load at a joint in a system, the method comprising steps of:
obtaining kinematic data for the system;
computing a modified acceleration using at least the kinematic data, wherein the modified acceleration is computed without using accelerations estimated from measured kinematics;
performing an inverse dynamics analysis to determine the estimated joint load, wherein the inverse dynamics analysis uses at least the modified acceleration; and
performing a forward dynamics analysis using the estimated joint load to determine simulated kinematic data for the system.

20. The method of claim 19, further comprising determining an input force for the system, wherein the inverse dynamics analysis further uses the input force to determine the estimated joint load.

21. The method of claim 20, wherein the input force comprises a ground reaction force.

22. The method of claim 19 wherein the step of computing the modified acceleration further comprises the steps of:
computing an error value representing a difference between the simulated kinematic data and the kinematic data; and
applying a feedback gain to the error value.

* * * * *